(12) United States Patent
Stoessel et al.

(10) Patent No.: US 8,124,249 B2
(45) Date of Patent: Feb. 28, 2012

(54) MATERIALS FOR ORGANIC ELECTROLUMINESCENT DEVICES

(75) Inventors: Philipp Stoessel, Frankfurt am Main (DE); Esther Breuning, Niedernhausen (DE); Amir Hossain Parham, Frankfurt am Main (DE)

(73) Assignee: Merck Patent GmbH, Darmstadt (DE)

( * ) Notice: Subject to any disclaimer, the term of this patent is extended or adjusted under 35 U.S.C. 154(b) by 802 days.

(21) Appl. No.: 11/908,641

(22) PCT Filed: Mar. 3, 2006

(86) PCT No.: PCT/EP2006/001991
§ 371 (c)(1),
(2), (4) Date: Sep. 14, 2007

(87) PCT Pub. No.: WO2006/097208
PCT Pub. Date: Sep. 21, 2006

(65) Prior Publication Data
US 2008/0171225 A1    Jul. 17, 2008

(30) Foreign Application Priority Data
Mar. 16, 2005   (EP) .................................. 05005709

(51) Int. Cl.
*C09K 11/06* (2006.01)
(52) U.S. Cl. .......................................... 428/690; 585/27
(58) Field of Classification Search ................. 428/690, 428/917; 585/27
See application file for complete search history.

(56) References Cited

U.S. PATENT DOCUMENTS

| | | | |
|---|---|---|---|
| 7,223,484 B2 | 5/2007 | Stössel et al. | |
| 2002/0021088 A1* | 2/2002 | Howard et al. | 313/504 |
| 2003/0230238 A1* | 12/2003 | Papadimitrakopoulos et al. | 118/715 |
| 2006/0043858 A1 | 3/2006 | Ikeda et al. | |

FOREIGN PATENT DOCUMENTS

| | | |
|---|---|---|
| DE | 10229370 A1 | 1/2004 |
| JP | 2000038353 | 2/2000 |
| JP | 2002280179 | 9/2002 |
| WO | WO-2004018587 A1 | 3/2004 |

OTHER PUBLICATIONS

Koepf et. al., Synthesis . . . Phenanthroline Strapped Porphyrin, 2005, Tetrahedron Letters, vol. 46, p. 139-142.*
Paul et. al, Design and Synthesis . . . Imidazole Recognition, 2002, Inorganic Chem., 2002, vol. 41, p. 3699-3704.*
Joachin et al., Balancing a four-branch-single-molecule Nanoscale Wheatstone bridge, 2003, Nanotechnology, vol. 14, pp. 283-289.*
Chambron et al., "Effect of the Spacer Moiety on the Rates of Electron Transfer with Bis-Porphyrin-Stoppered Rotaxanes", *J. Am. Chem. Soc.*, vol. 115, pp. 7419-7425 (1993).
Chambron, et al., "Construction of porphyrin-containing rotaxanes for long-range photoinduced charge separation", *C. R. Acad. Sci. Paris*, vol. 323, pp. 483-492 (1996).
Armaroli, et al., "Protonation of free 2,9-bis(p-biphenylyl)-1,10-phenanthroline sites in a 56-membered macrocycle and in its $Re^I$ and $Cu^I$ complexe—absorption spectra, luminesence properties, and excited state interactions", *J. Chem. Soc., Faraday Trans.*, vol. 93, pp. 4145-4150 (1997).
Andersson, et al., "Long-Range Electron Transfer in Porphyrin-Containing [2]-Rotxanes: Tuning the Rate by Metal Cation Coordination", *J. Am. Chem. Soc.*, vol. 124, pp. 4347-4362 (2002).
Koepf, et al., "Synthesis of a highly soluble superstructured phenanthroline strapped porphyrin", *Tetrahedron Letters*, vol. 46, pp. 139-142 (2005).

* cited by examiner

*Primary Examiner* — D. Lawrence Tarazano
*Assistant Examiner* — Gregory Clark
(74) *Attorney, Agent, or Firm* — Connolly Bove Lodge & Hutz LLP

(57) ABSTRACT

The present invention relates to novel materials which can be used in organic electronic devices, in particular electroluminescent devices, and are derivatives of fused aromatic systems.

12 Claims, No Drawings

MATERIALS FOR ORGANIC ELECTROLUMINESCENT DEVICES

RELATED APPLICATIONS

This application is a national stage application (under 35 U.S.C. §371) of PCT/EP2006/001991, filed Mar. 3, 2006, which claims benefit of European application 050 057 09.0, filed Mar. 16, 2005.

The present invention relates to novel materials which can be used in organic electronic devices, in particular electroluminescent devices, and which are derivatives of fused aromatic systems.

In a number of applications of various types which can be ascribed to the electronics industry in the broadest sense, the use of organic semi-conductors as functional materials has been reality for some time or is expected in the near future, for example in organic electroluminescent devices (OLEDs).

However, these devices always still exhibit considerable problems requiring urgent improvement:
1. The operating lifetime is always still short, in particular in the case of blue emission, meaning that it has hitherto only been possible to achieve simple applications commercially.
2. In some cases, use is made of mixtures of isomeric compounds, which may have different physical properties (glass transition temperature, glass formation properties, absorption, photoluminescence). Since these stereoisomers in some cases also have different vapour pressures at the processing temperature, uniform, reproducible production of the organic electronic device is not possible. This problem is described in detail, for example, in unpublished application EP 04026402.0.
3. The compounds used are in some cases only sparingly soluble in common organic solvents, which makes their purification during synthesis more difficult, but also makes cleaning of the plants in the case of the production of the organic electronic devices more difficult.

The closest prior art can be regarded as the use of various fused aromatic compounds, in particular anthracene or pyrene derivatives, as host materials, in particular for blue-emitting electroluminescent devices. The host material disclosed in the prior art is 9,10-bis(2-naphthyl)anthracene (U.S. Pat. No. 5,935,721). Further anthracene derivatives which are suitable as host materials are described, for example, in WO 01/076323, WO 01/021729, WO 04/013073, WO 04/018588, WO 03/087023 or WO 04/018587. Host materials based on aryl-substituted pyrenes and chrysenes are described in WO 04/016575, which in principle also encompasses corresponding anthracene and phenanthrene derivatives. WO 03/095445 and CN 1362464 describe 9,10-bis(1-naphthyl)anthracene derivatives for use in OLEDs. Although good results have already been achieved with these compounds, it would be desirable to have improved host materials available. The above-mentioned compounds are particularly problematical if they form atropisomers and thus lead to poorly reproducible results during device production.

The above-mentioned prior art confirms that the host material plays a crucial role in the function of organic electroluminescent devices. It should therefore be possible further to improve the properties of the organic electronic devices by optimisation of the materials. Thus, there continues to be a demand for materials, in particular host materials for blue-emitting OLEDs, which lead to good efficiencies and at the same time to long service lives in organic electronic devices and lead to reproducible results in the production and operation of the devices. Surprisingly, it has been found that organic electronic devices which contain macrocyclic compounds containing certain fused aromatic rings have significant improvements over the prior art. These materials enable an increase in the efficiency and lifetime in the organic electronic device compared with materials in accordance with the prior art. Since these materials cannot exhibit atropisomerism, reproducible production of the organic electronic devices continues to be possible. The present invention therefore relates to these materials and to the use thereof in organic electronic devices.

JP 05140145 describes certain macrocyclic compounds for use in OLEDs. These compounds are described as luminescent materials or as hole-transport compounds. The suitability of macrocyclic compounds of this type as host materials is not evident from this application.

The invention relates to compounds of the formula (1)

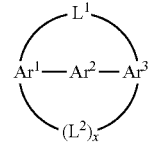

formula (1)

where the following applies to the symbols and indices used:

$Ar^1$, $Ar^3$ is on each occurrence, identically or differently, an aromatic or heteroaromatic ring system having 5 to 50 aromatic ring atoms, which may be substituted by one or more radicals R;

$Ar^2$ is on each occurrence, identically or differently, a fused aryl or heteroaryl group having 14 to 40 aromatic ring atoms, which may be substituted by one or more radicals R, with the proviso that the two groups $Ar^1$ and $Ar^3$ are not linked to $Ar^2$ via adjacent positions or peri-positions;

$L^1$, $L^2$ is on each occurrence, identically or differently, a divalent organic bridge containing 1 to 60 C atoms, which may be substituted by one or more radicals R;

R is on each occurrence, identically or differently, H, F, Cl, Br, I, CN, $NO_2$, $COOR^1$, $B(OR^1)_2$, $B(R^1)_2$, $Si(R^1)_3$, a straight-chain alkyl or alkoxy chain having 1 to 40 C atoms or a branched or cyclic alkyl or alkoxy group having 3 to 40 C atoms, each of which may be substituted by $R^1$ and in which one or more non-adjacent C atoms may be replaced by N—$R^1$, O, S, O—CO—O, CO—O, —$CR^1$=$CR^1$— or —C≡C— and in which, in addition, one or more H atoms may be replaced by F, Cl, Br, I or CN, or an aromatic or heteroaromatic ring system having 5 to 40 aromatic ring atoms, which may be substituted by one or more radicals $R^1$, or a combination of two, three or four of these systems; two or more radicals R here may with one another also form a further mono- or polycyclic, aliphatic or aromatic ring system;

$R^1$ is on each occurrence, identically or differently, H or an aliphatic or aromatic hydrocarbon radical having 1 to 20 C atoms; two or more radicals $R^1$ here may also with one another form a ring system;

x is on each occurrence, identically or differently, 0 or 1, where x=0 means that bridge $L^2$ is not present.

The compound of the formula (1) preferably has a glass transition temperature $T_g$ of above 70° C., particularly preferably above 100° C., very particularly preferably above 130° C.

For the purposes of this invention, an aromatic ring system contains 6 to 40 C atoms in the ring system. For the purposes of this invention, a heteroaromatic ring system contains 2 to 40 C atoms and at least one heteroatom in the ring system, with the proviso that the total number of C atoms and heteroatoms is at least 5. The heteroatoms are preferably selected from N, O and/or S. For the purposes of this invention, an aromatic or heteroaromatic ring system is taken to mean a system which does not necessarily contain only aryl or heteroaryl groups, but in which a plurality of aryl or heteroaryl groups may also be interrupted by a short non-aromatic unit (less than 10% of the atoms other than H, preferably less than 5% of the atoms other than H), such as, for example, an $sp^3$-hybridised C, N or O atom. Thus, for example, aromatic ring systems for the purposes of this invention are also taken to mean systems such as 9,9'-spirobifluorene, 9,9-diarylfluorene, triarylamine, diaryl ether, etc. Part of the aromatic or heteroaromatic ring system here may also be a fused group in the sense of the following definition.

For the purposes of this invention, a fused aryl or heteroaryl group is taken to mean a ring system having 9 to 40 aromatic ring atoms in which at least two aromatic or heteroaromatic rings are fused to one another, i.e. have at least one common edge and a common aromatic π-electron system. These ring systems may be substituted by R or unsubstituted. Examples of fused aromatic or heteroaromatic ring systems are naphthalene, quinoline, anthracene, phenanthrene, pyrene, perylene, chrysene, acridine, etc., while biphenyl, for example, is not a fused aryl group since there is no common edge between the two ring systems therein. Fluorene, for example, is likewise not a fused aromatic ring system since the two phenyl units therein do not form a common aromatic ring system.

For the purposes of this invention, adjacent positions, which are excluded for the linking of $Ar^2$, are taken to mean positions on two directly adjacent C atoms of the aromatic ring. For the purposes of this invention, the peri-position is taken to mean the 1,8-position in naphthalene or comparable positions in other fused aryl or heteroaryl groups.

For the purposes of the present invention, a $C_1$- to $C_{40}$-alkyl group, in which individual H atoms or $CH_2$ groups may also be substituted by the above-mentioned groups, is particularly preferably taken to mean the radicals methyl, ethyl, n-propyl, i-propyl, n-butyl, i-butyl, s-butyl, t-butyl, 2-methylbutyl, n-pentyl, s-pentyl, cyclopentyl, n-hexyl, cyclohexyl, n-heptyl, cycloheptyl, n-octyl, cyclooctyl, 2-ethylhexyl, trifluoromethyl, pentafluoro-ethyl, 2,2,2-trifluoroethyl, ethenyl, propenyl, butenyl, pentenyl, cyclopentenyl, hexenyl, cyclohexenyl, heptenyl, cycloheptenyl, octenyl, cyclo-octenyl, ethynyl, propynyl, butynyl, pentynyl, hexynyl or octynyl. A $C_1$- to $C_{40}$-alkoxy group is particularly preferably taken to mean methoxy, ethoxy, n-propoxy, i-propoxy, n-butoxy, i-butoxy, s-butoxy, t-butoxy or 2-methyl-butoxy. An aromatic or heteroaromatic ring system having 5-30 aromatic ring atoms, which may also in each case be substituted by the above-mentioned radicals R and which may be linked to the aromatic or hetero-aromatic ring via any desired positions, is in particular taken to mean groups derived from benzene, naphthalene, anthracene, phenanthrene, pyrene, chrysene, perylene, fluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,3-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

The fused aryl or heteroaryl group $Ar^2$ preferably contains three, four, five or six aromatic or heteroaromatic units, which are in each case fused to one another via one or more common edges and thus form a common aromatic π-electron system and which may be substituted by R or unsubstituted. The fused aryl or heteroaryl group $Ar^2$ particularly preferably contains three, four or five aromatic or heteroaromatic units, in particular three or four aromatic or heteroaromatic units, which are in each case fused to one another via one or more common edges and thus form a common aromatic system and which may be substituted by R or unsubstituted. The mutually fused aromatic and heteroaromatic units are preferably selected from benzene, pyridine, pyrimidine, pyrazine and pyridazine, which may be substituted by R or unsubstituted, particularly preferably benzene and pyridine, very particularly preferably benzene. Scheme 1 below shows diagrammatically with reference to the example of anthracene what is meant by aromatic units and common edges in a fused aryl group.

Scheme 1

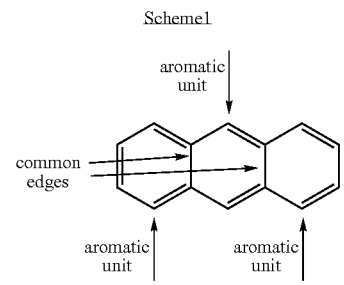

The two groups $Ar^1$ and $Ar^3$ here are not linked to $Ar^2$ via adjacent positions and not via peri-positions. The linking preferably occurs in such a way that at least four aromatic ring atoms of unit $Ar^2$ are located between the linking of $Ar^1$ and $Ar^2$.

The fused aryl or heteroaryl groups $Ar^2$ are particularly preferably selected from the group consisting of anthracene, acridine, phenanthrene, phenanthroline, pyrene, naphthacene, chrysene, pentacene and perylene, which may optionally be substituted by R. Substitution by R may be appropriate in order to obtain more highly soluble compounds. The fused aromatic ring systems are particularly preferably selected from the group consisting of anthracene, phenanthrene, pyrene and perylene, in particular anthracene and pyrene, which may optionally be substituted by R. The units $Ar^1$ and $Ar^3$ are preferably linked to anthracene via the 1,5-position, the 9,10-position, the 2,6-position or via the 1,4-position, particularly preferably via the 9,10-position. The linking to pyrene preferably takes place via the 1,6-, 1,8-, 173- or 2,7-position, particularly preferably via the 1,6- or via the 2,7-position. The linking to phenanthrene preferably takes place via the 2,7-, 3,6-, 2,9- or 2,10-position, particularly preferably via the 2,7- or via the 3,6-position. The linking to perylene preferably takes place via the 3,9-, 3,10-, 3,8- or 2,8-position, particularly preferably via the 3,9- or via the 3,10-position. The linking to phenanthroline preferably takes place via the 2,9- or via the 3,8-position. The positions on these fused aryl groups are shown in scheme 2 below.

Scheme 2

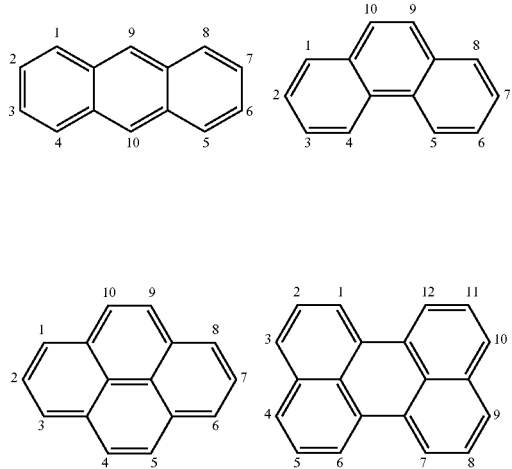

Preferred groups $Ar^1$ and $Ar^3$, identically or differently on each occurrence, are aromatic or heteroaromatic ring systems having 5 to 20 aromatic ring atoms, particularly preferably having 5 to 16 aromatic ring atoms, very particularly preferably having 6 to 14 aromatic ring atoms. These may each be substituted by R or unsubstituted. Particular preference is given to aromatic ring systems containing no aromatic heteroatoms. In a particularly preferred embodiment of the invention, bridge $L^1$ and, if present, bridge $L^2$ are linked to $Ar^1$ and $Ar^3$ respectively in the ortho-position to the link to $Ar^2$. The ortho position here is taken to mean, analogously to benzene, the position on directly adjacent carbon atoms.

Groups $Ar^1$ and $Ar^3$ are preferably selected to be identical. This preference is due to the easier synthetic accessibility of the compounds.

Preferred divalent bridges $L^1$ and $L^2$ are systems containing 1 to 60 C atoms, selected from the groups of the alkylenes, alkenes, aromatic groups containing 6 to 40 C atoms, heteroaromatic groups containing 2 to 40 C atoms, imines, alkoxy groups, thioalkoxy groups, aryloxy groups, thioaryl groups, amines, arylamines and arylboranes, or combinations of one or more of these systems. The combination of alkenes and aromatic compounds or heteroaromatic compounds is particularly preferred. Preference is furthermore given to arylamines, aryloxy groups or alkoxy groups. The bridges here may also each be substituted by the above-mentioned radicals R.

Bridges $L^1$ and $L^2$ are particularly preferably selected from divalent straight-chain alkylene groups containing 1 to 10 C atoms, or branched or cyclic alkylene groups containing 3 to 10 C atoms, divalent alkoxy or bialkoxy groups having 1 to 10 C atoms, divalent alkene groups, divalent aromatic ring systems having 6 to 20 C atoms, divalent heteroaromatic ring systems having 2 to 20 C atoms, or a combination of two, three or four of these systems. These groups may also be substituted by the above-mentioned radicals R. Bridges $L^1$ and $L^2$ are very particularly preferably selected from divalent straight-chain alkylene groups containing 1 to 8 C atoms, branched or cyclic alkylene groups containing 3 to 10 C atoms, divalent alkoxy or bialkoxy groups having 1 to 8 C atoms, divalent alkene groups, divalent aromatic ring systems having 6 to 18 C atoms, divalent heteroaromatic ring systems having 3 to 18 C atoms, or a combination of two or three of these systems.

The length of the bridge here is preferably selected so that substantially stress-free systems are formed. Depending on the length of the bridge, systems in which free rotation of group $Ar^2$ about the bond to $Ar^1$ and $Ar^3$ is possible or in which free rotation of group $Ar^2$ is not possible may be formed.

The bridge length is preferably selected so that the bridge contains 4 to 20 bridge atoms in the direct connection. The bridge length or direct connection is taken to mean the shortest path along the bridge atoms between the linking points. It should be noted here that the number of bridge atoms is greater than the bridge length since only the atoms of the direct connections are considered in the bridge length. If $Ar^2$ is a 9,10- or 1,4-linked anthracene unit, the bridge preferably contains 4 to 14 bridge atoms, particularly preferably 5 to 8 bridge atoms. If $Ar^2$ is a pyrene unit or a 2,7-linked phenanthrene unit, the bridge preferably contains 5 to 16 bridge atoms, particularly preferably 7 to 14 bridge atoms. If $Ar^2$ is a 3,6-linked phenanthrene unit, the bridge preferably contains 4 to 12 bridge atoms, particularly preferably 4 to 10 bridge atoms.

In a preferred embodiment of the invention, the index x=0, i.e. only one bridge $L^1$ is present. This may be preferred, since compounds of lower molecular weight are then formed, which can be evaporated more easily or are more highly soluble.

In a further preferred embodiment of the invention, the index x=1, i.e. two bridges $L^1$ and $L^2$ are present in the structure. This may be preferred, since compounds of this type are easier to synthesise in some cases.

The compounds of the formula (1) or the bridge(s) here may also be charged.

Examples of suitable compounds of the formula (1) are the structures (1) to (82) shown below.

(1)
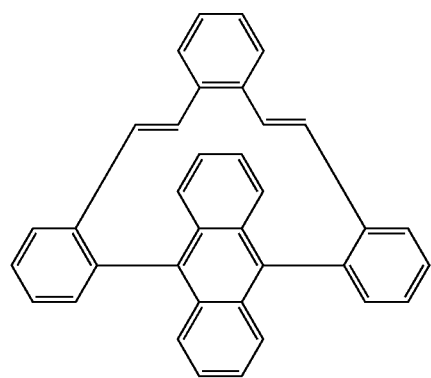
(2)
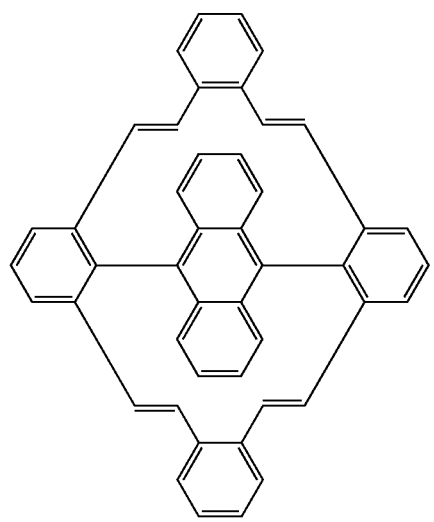
(3)
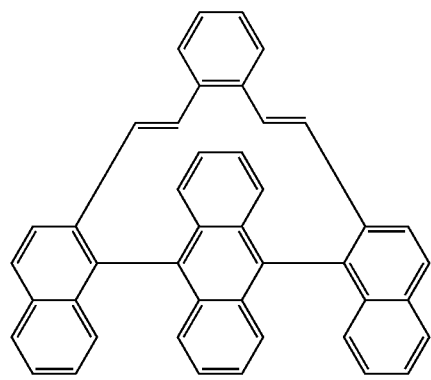
(4)
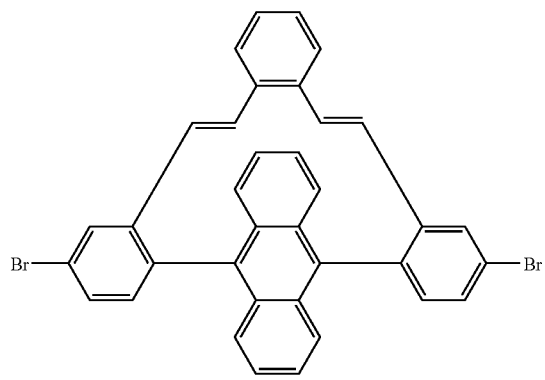
(5)
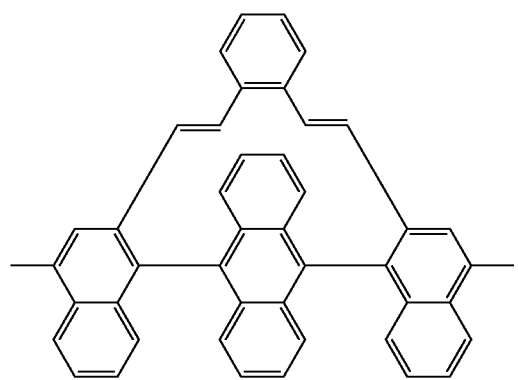
(6)
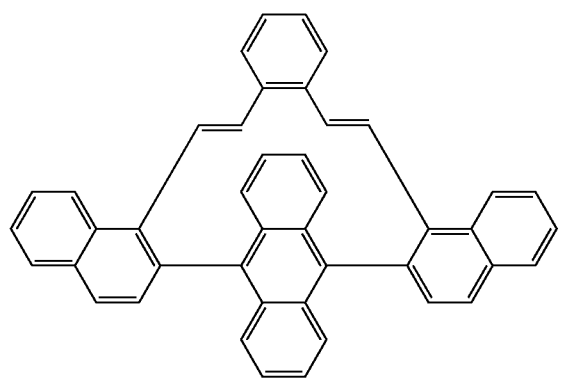
(7)
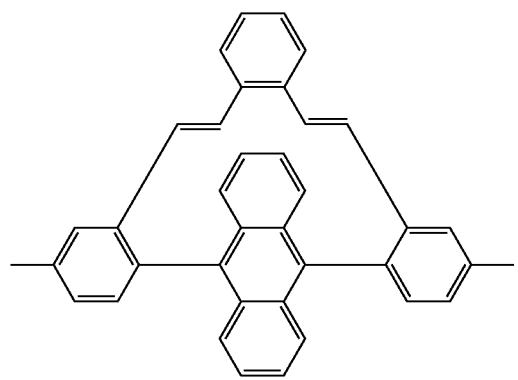
(8)
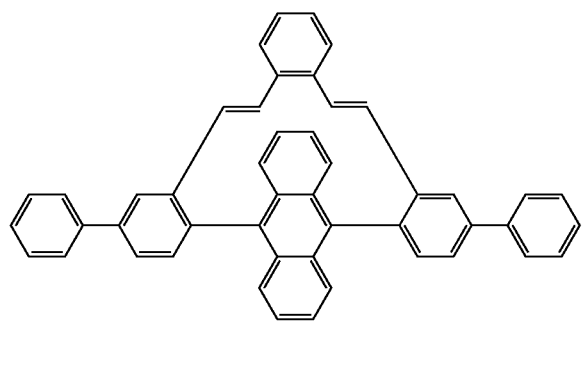

-continued
(9)
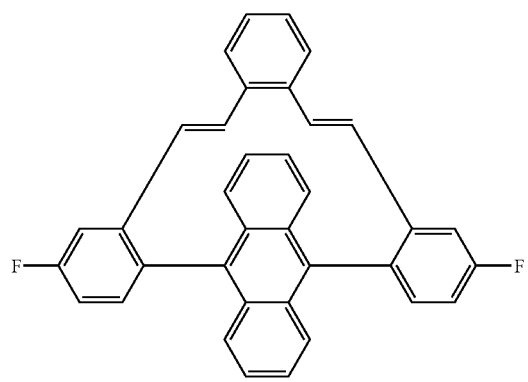
(10)
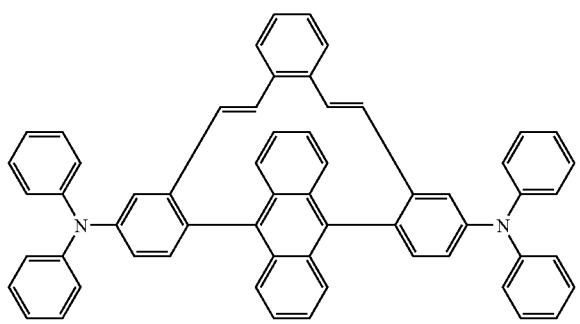
(11)
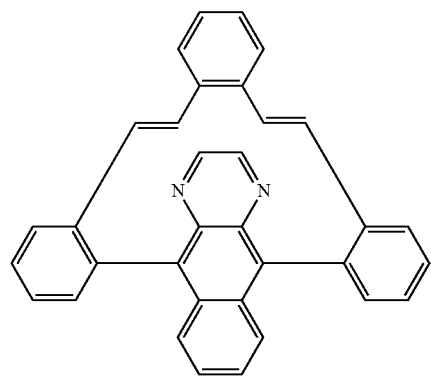
(12)
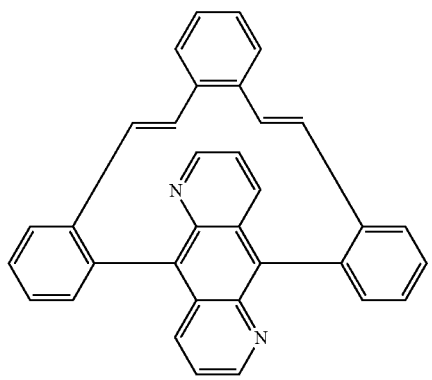
(13)
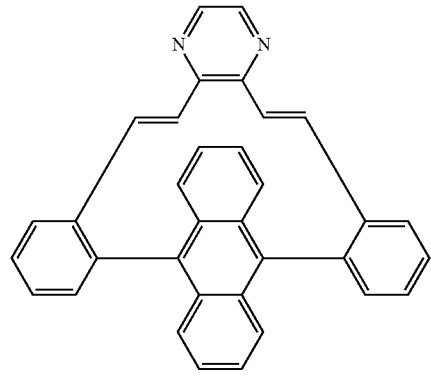
(14)
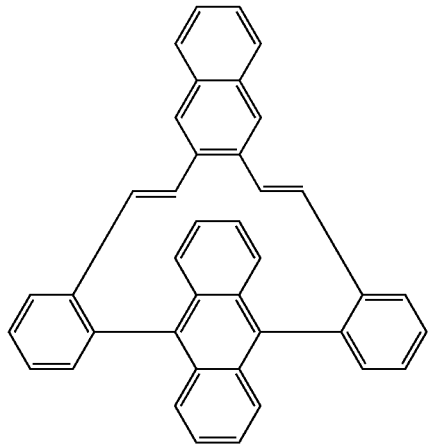
(15)
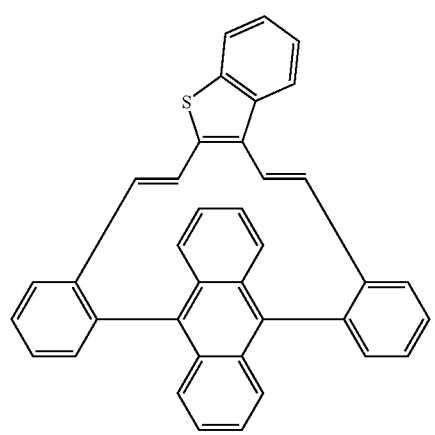
(16)
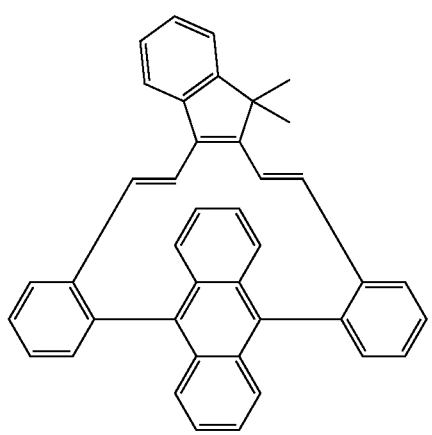

-continued
(17)
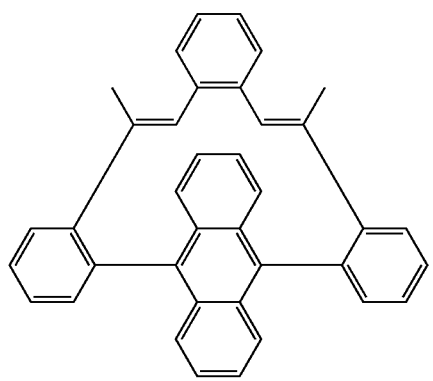
(18)
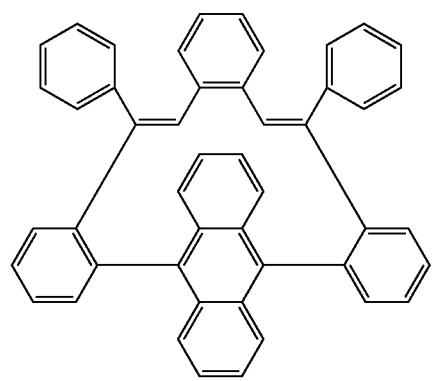
(19)
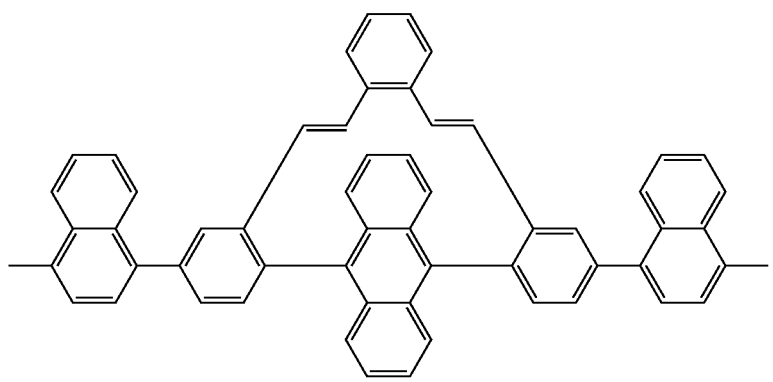
(20)
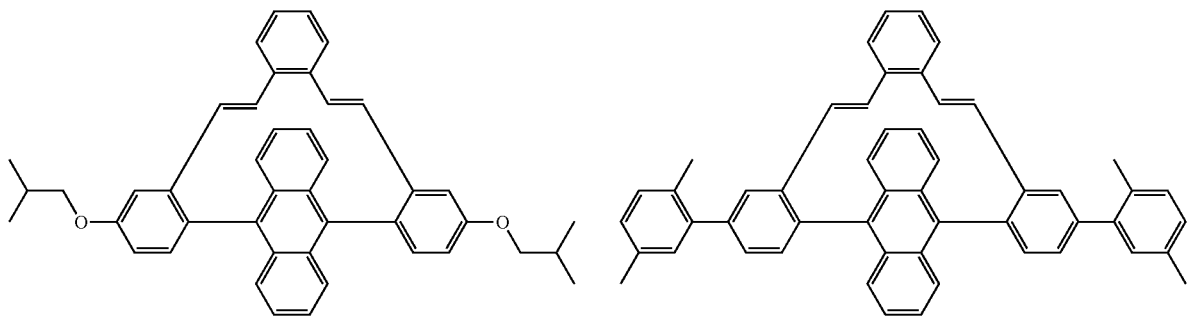
(21)
(22)
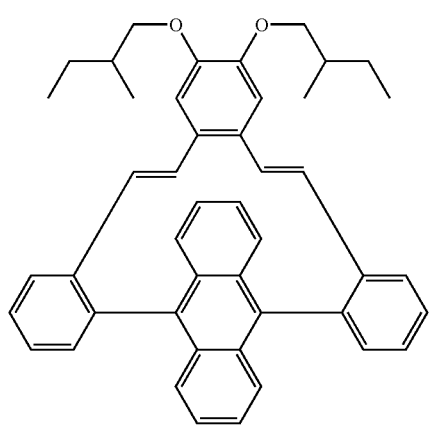
(23)
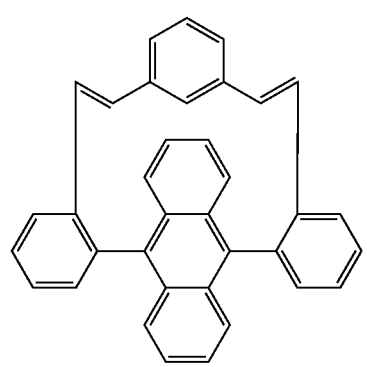

(24)
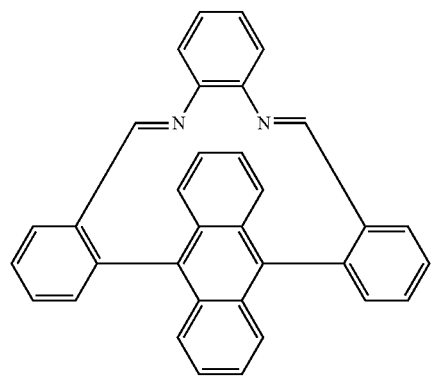
(25)
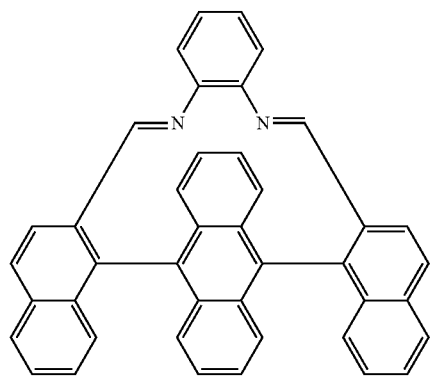
(26)
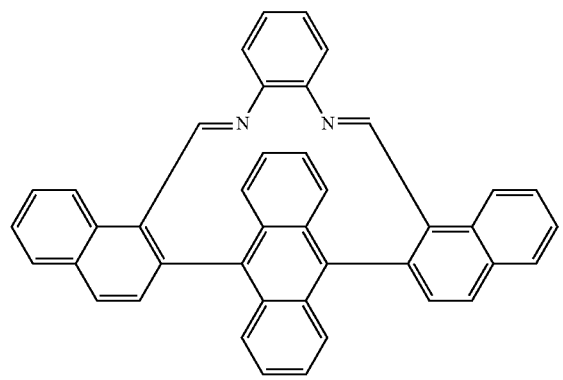
(27)
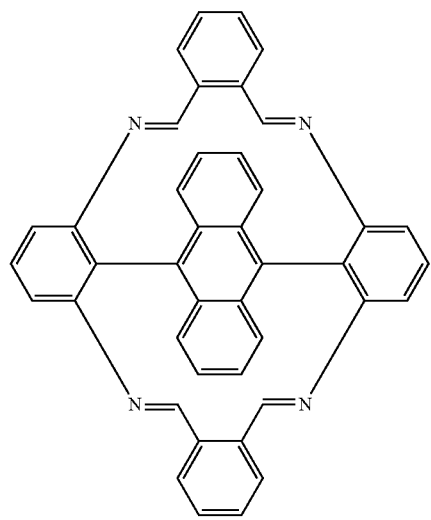
(28)
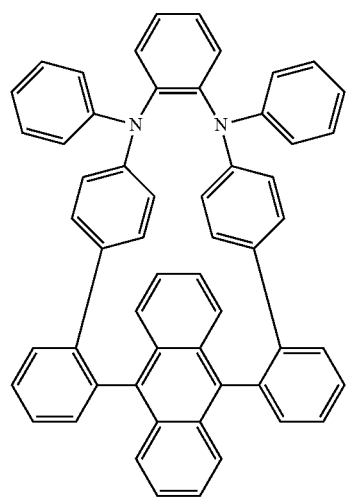
(29)
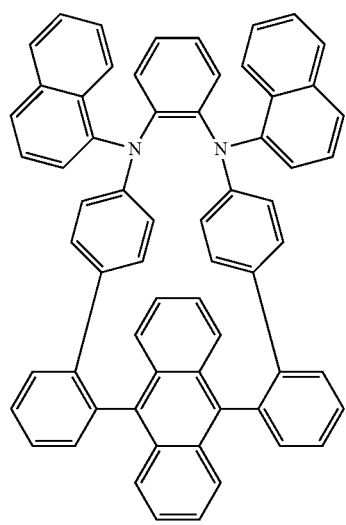

(30)
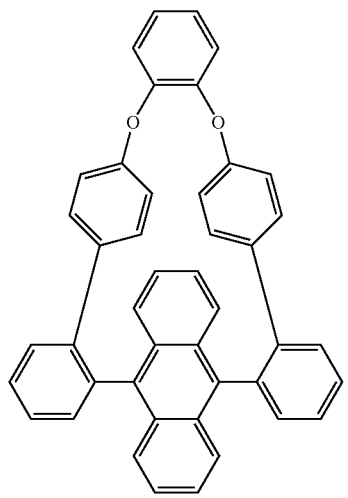
(31)
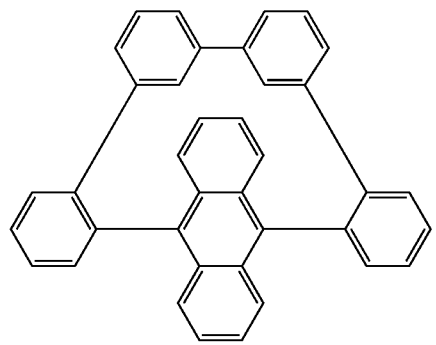
(32)
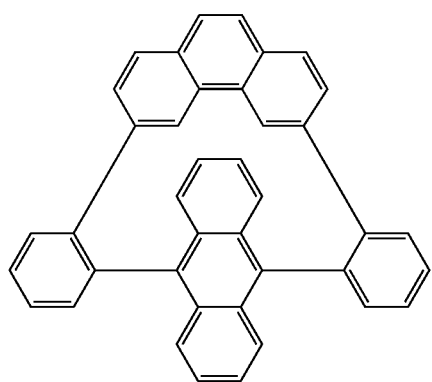
(33)
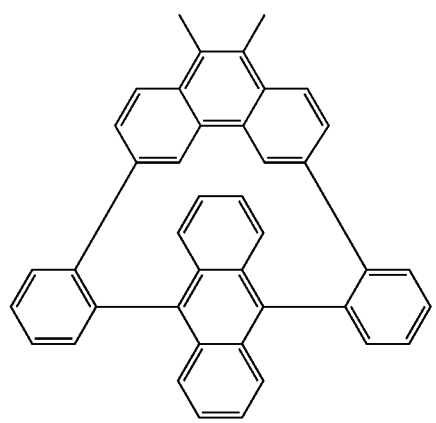
(34)
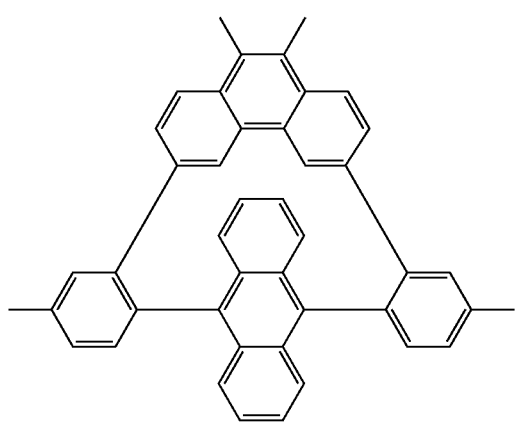
(35)
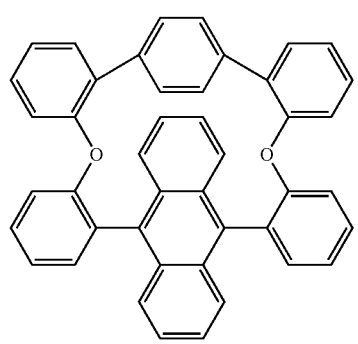

-continued
(36)
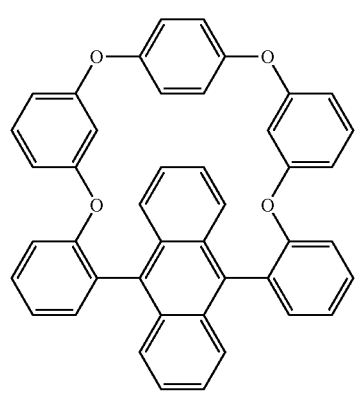
(37)
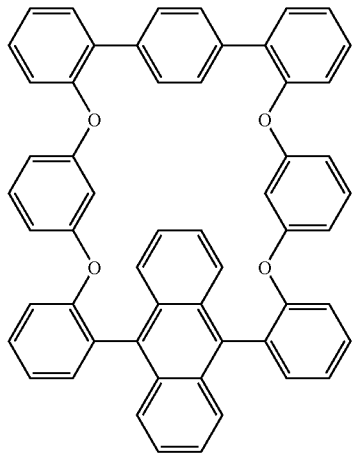
(38)
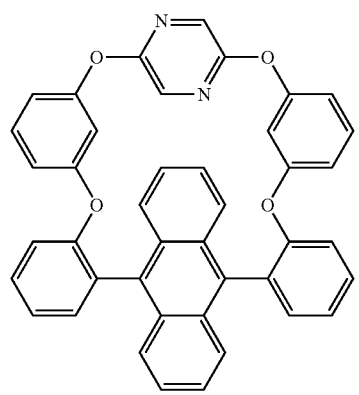
(39)
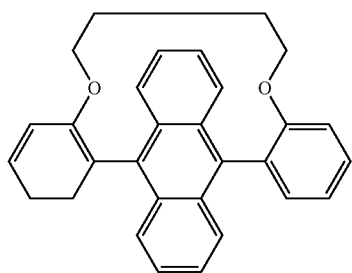
(40)
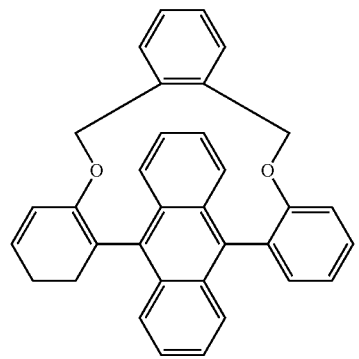
(41)
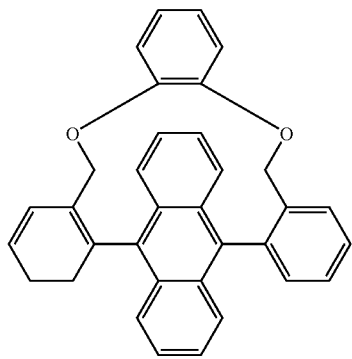
(42)
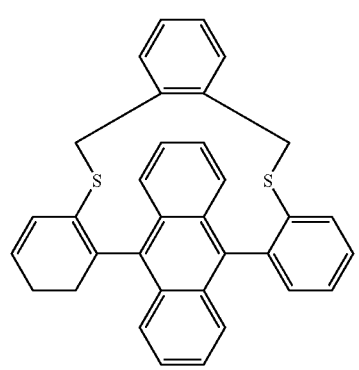
(43)
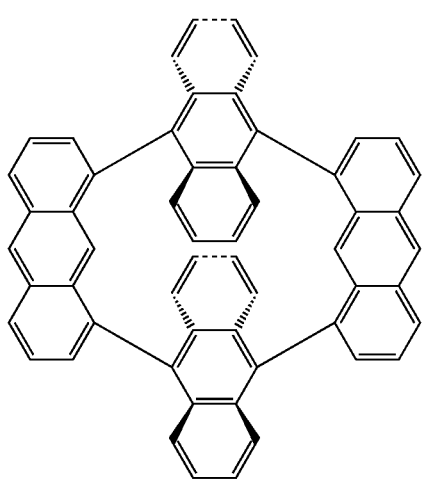

-continued
(44)
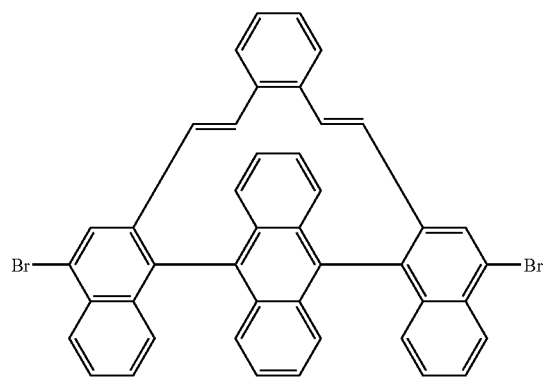
(45)
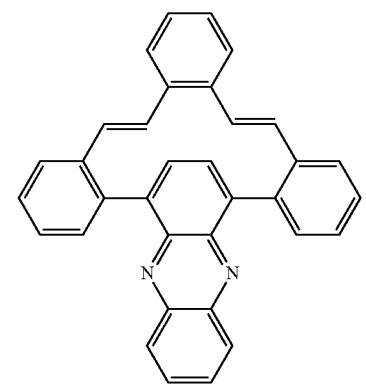
(46)
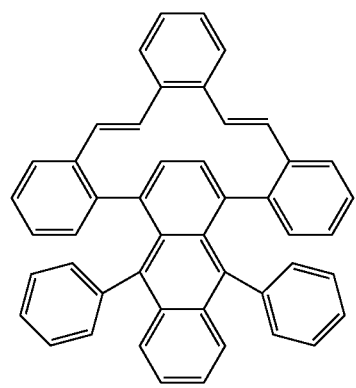
(47)
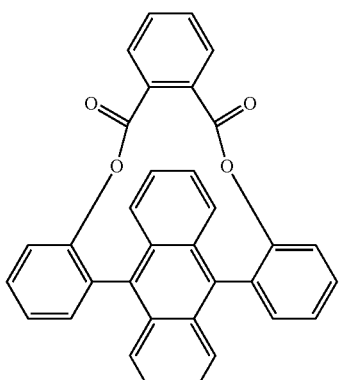
(48)
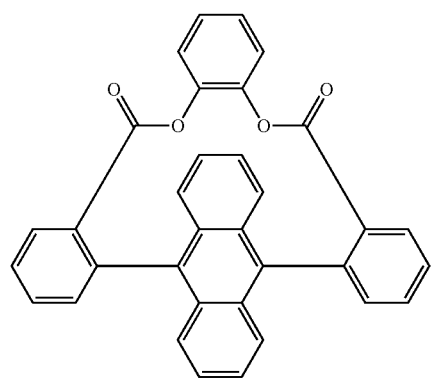
(49)
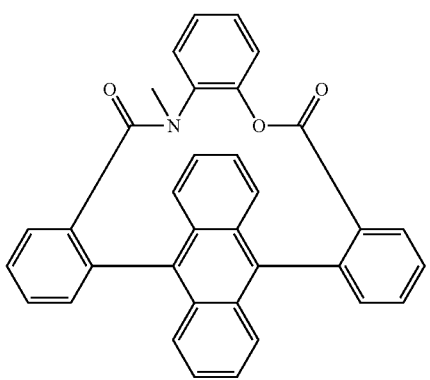
(50)
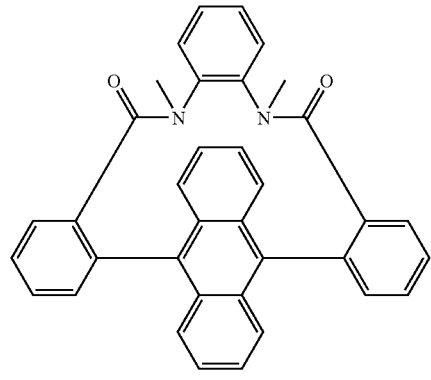
(51)
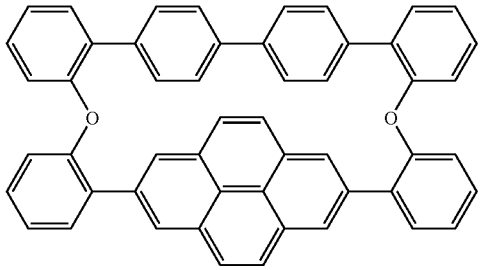

-continued
(52)
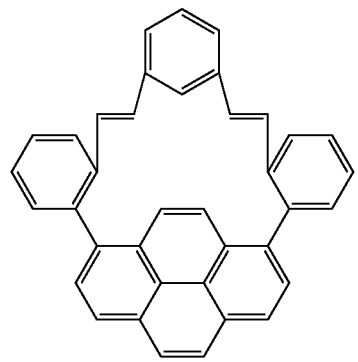
(53)
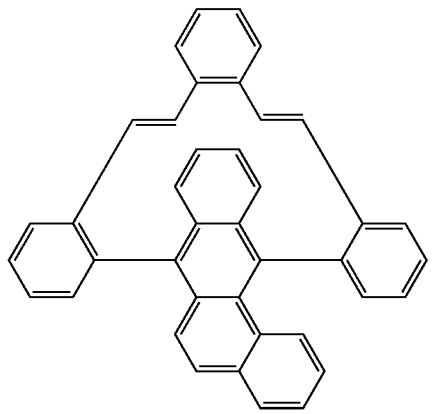
(54)
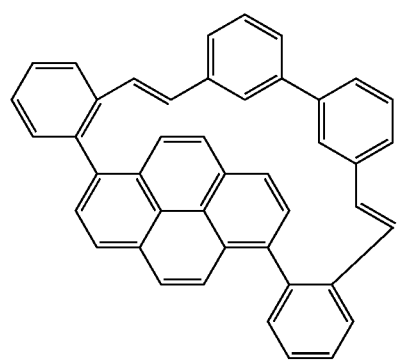
(55)
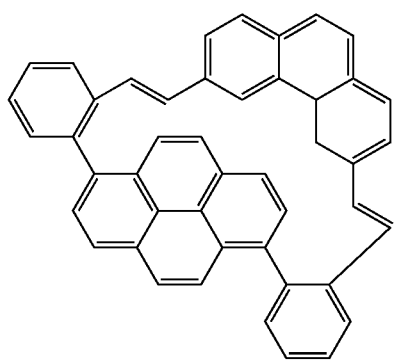
(56)
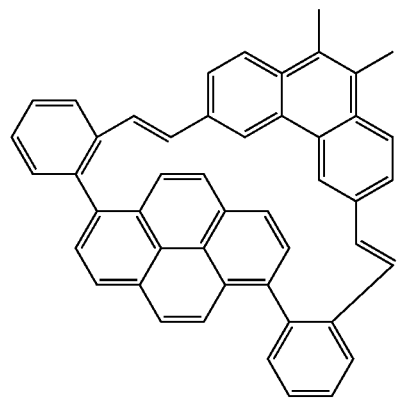
(57)
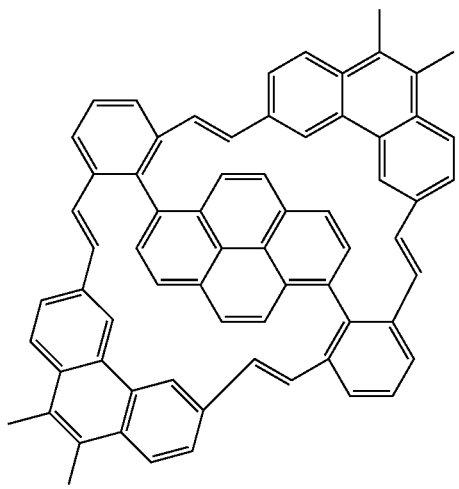
(58)
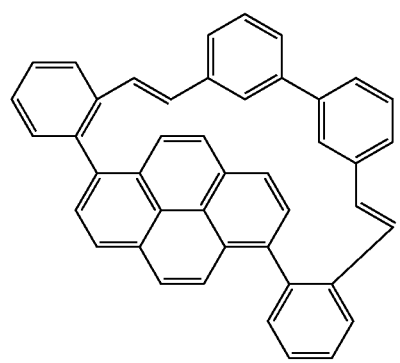
(59)
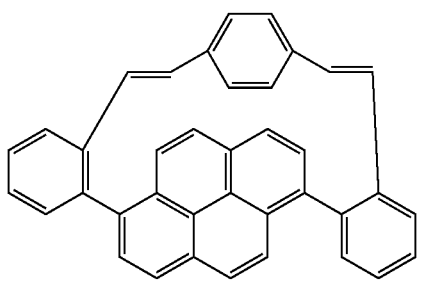

-continued
(60)
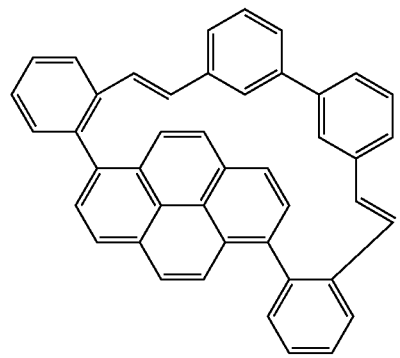
(61)
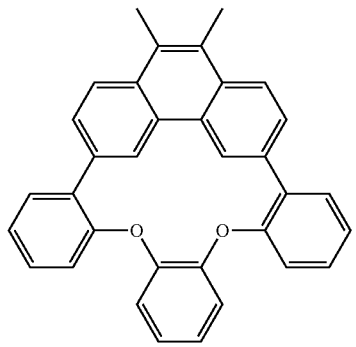
(62)
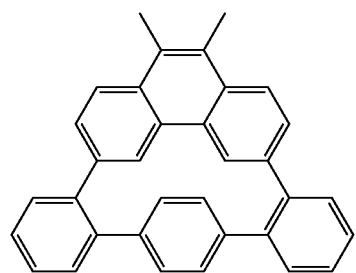
(63)
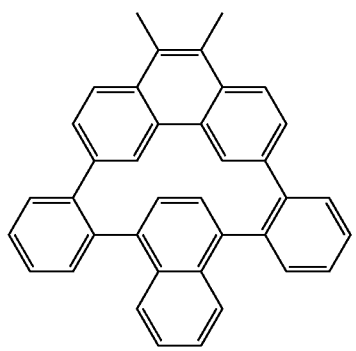
(64)
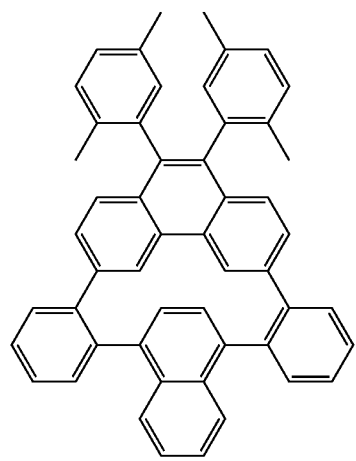
(65)
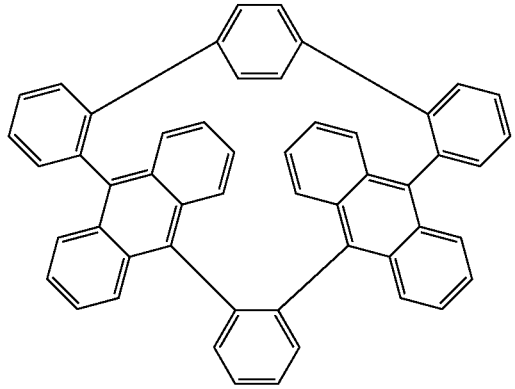
(66)
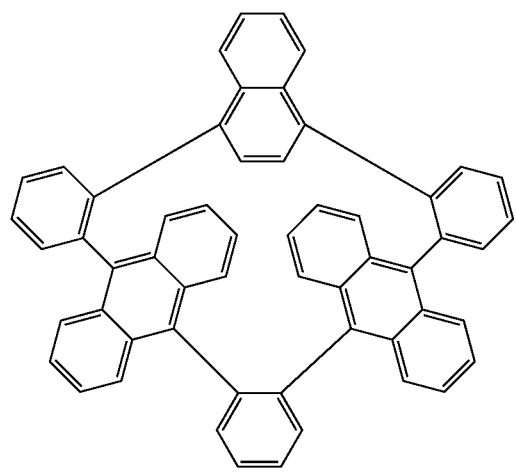
(67)
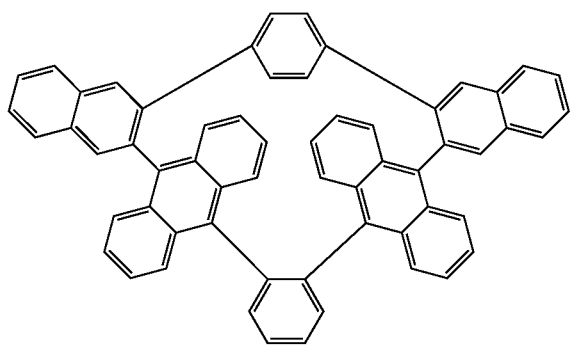

-continued
(68)
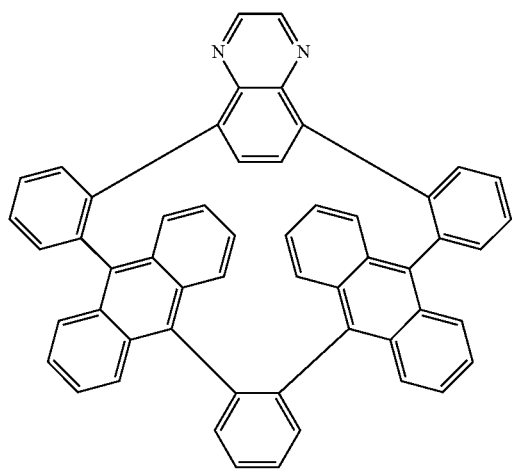
(69)
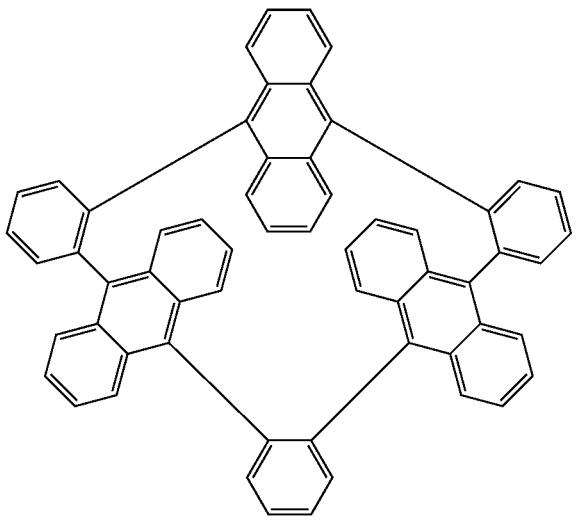
(70)
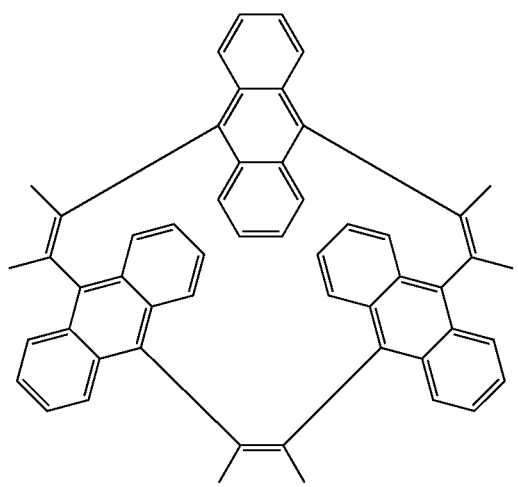
(71)
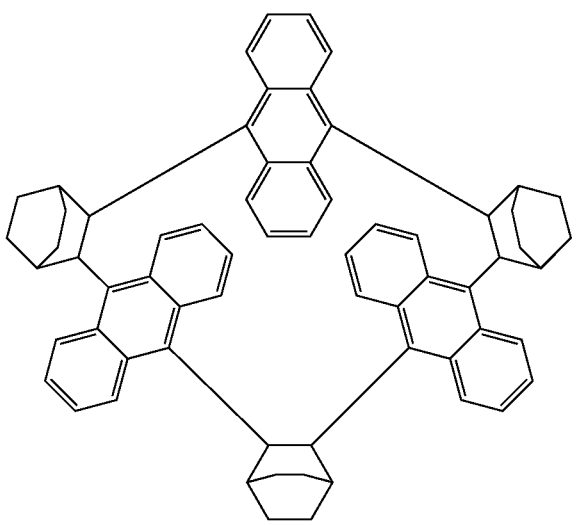
(72)
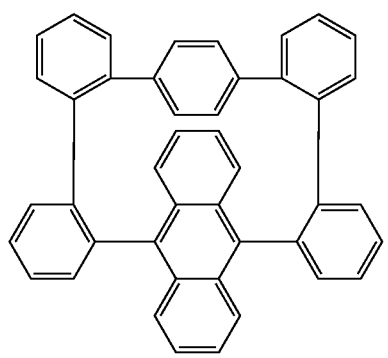
(73)
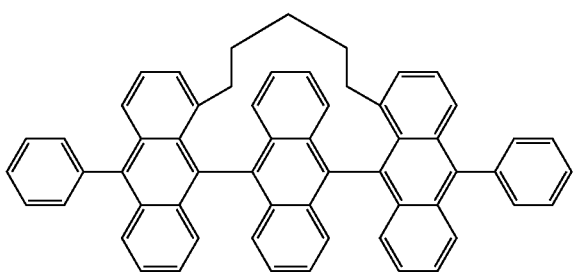

-continued
(74)
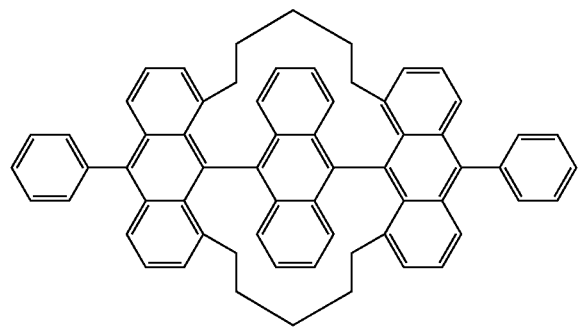
(75)
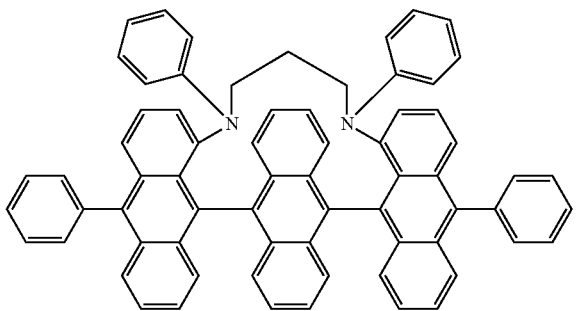
(76)
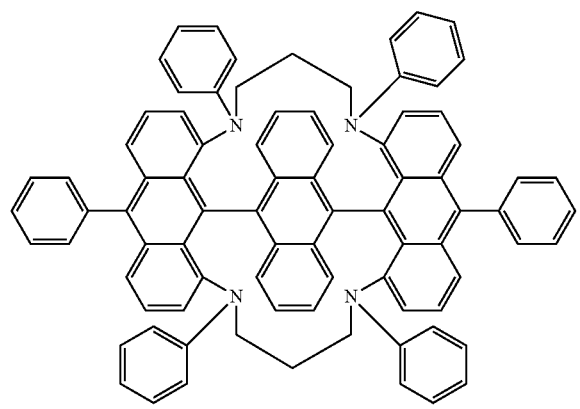
(77)
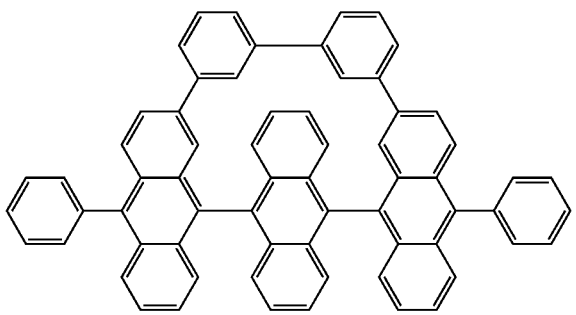
(78)
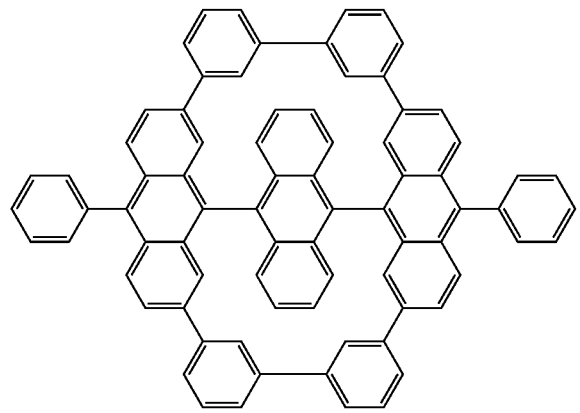
(79)
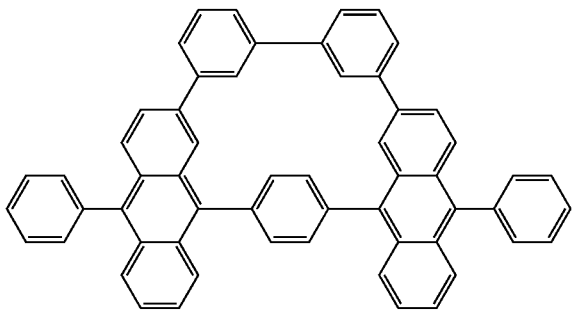
(80)
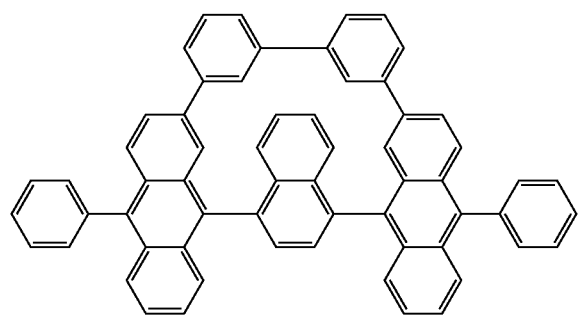
(81)
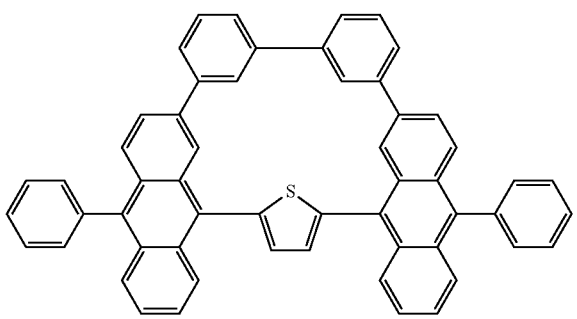

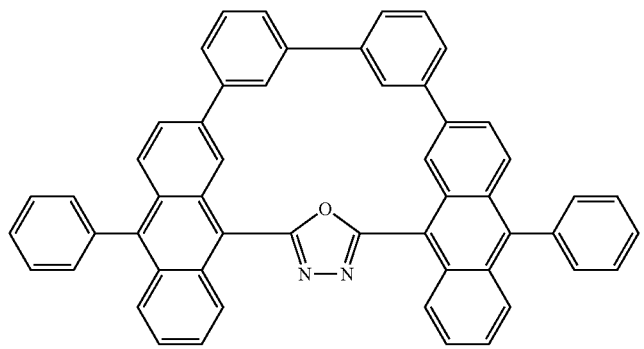

(82)

For the general syntheses of compounds of the formula (1), reference is made to B. Dietrich, P. Viout, J.-M. Lehn (*Macrocyclic Chemistry*, 1992, VCH). Compounds of the formula (1) can be synthesised, for example, by firstly constructing an $Ar^1$-$Ar^2$-$Ar^3$ system which carries on aromatic groups $Ar^1$ and $Ar^3$ suitable functionalities which facilitate formation of bridges $L^1$ and $L^2$ respectively. In a further reaction step, bridge $L^1$ or both bridges $L^1$ and $L^2$ can then be introduced. If the structure is such that rotation about the $Ar^1$-$Ar^2$ bond and about the $Ar^1$-$Ar^3$ bond is hindered (presence of atropisomers), it may be appropriate firstly to isolate the atropisomer in which the two functional groups are on the same side of $Ar^2$ (syn isomer). This can be achieved, for example, by recrystallisation or by chromatographic separation (see, for example, EP 04026402.0). This enables the formation of bridge $L^1$ and the ring closure to be carried out more simply. For the introduction of the bridge, it may be appropriate to carry out the reaction with dilution in order to simplify the ring closure and to prevent the formation of oligomers or polymers. Various types of reaction which are suitable for the formation of bridge $L^1$ and optionally $L^2$ are, for example, the Wittig-Horner reaction, imine formation, ether formation, for example by the Williamson method or by the palladium-catalysed Buchwald method, Claisen ester condensation, Ziegler nitrile condensation, acyloin condensation, Ruzicka condensation of carboxylic acid salts of cerium or of thorium, ester formation, amide formation, 4+2 cycloaddition, for example Diels-Alder reaction, Buchwald amination, Suzuki coupling or olefin metathesis.

Suitably functionalised compounds of the formula (1), in particular brominated compounds, such as, for example, the structures (4) and (44) shown above, can also be used for incorporation into polymers.

The invention therefore furthermore relates to conjugated, partially conjugated or non-conjugated polymers, oligomers or dendrimers containing repeating units of the formula (1). These repeating units can, for example, be polymerised into polyfluorenes (for example in accordance with EP 842208 or WO 00/22026), polyspirobifluorenes (for example in accordance with EP 707020, EP 894107 or EP 04028865.6), poly-para-phenylenes (for example in accordance with WO 92/18552), polydihydrophenanthrenes (for example in accordance with WO 014689), polyphenanthrenes (for example in accordance with WO 05/104264), polyindenofluorenes (for example in accordance with WO 04/041901 or WO 04/113412), polycarbazoles (for example in accordance with WO 04/070772), polyanthracenes, polynaphthalenes or polythiophenes (for example in accordance with EP 1028136). Polymers containing a plurality of these units or homopolymers of the repeating units of the formula (1) are also possible.

The invention furthermore relates to mixtures comprising at least one compound of the formula (1) and one or more compounds selected from the class of the monostyrylamines, distyrylamines, tristyrylamines, tetrastyrylamines and arylamines. A monostyrylamine is taken to mean a compound which contains one styryl group and at least one, preferably aromatic, amine. A distyrylamine is taken to mean a compound which contains two styryl groups and at least one, preferably aromatic, amine. A tristyrylamine is taken to mean a compound which contains three styryl groups and at least one, preferably aromatic, amine. A tetrastyrylamine is taken to mean a compound which contains four styryl groups and at least one, preferably aromatic, amine. For the purposes of this invention, an arylamine or an aromatic amine is taken to mean a compound which contains three aromatic or heteroaromatic ring systems bonded directly to the nitrogen. The styryl groups are particularly preferably stilbenes, which may also be further substituted Particularly preferred dopants are selected from the class of the tristyrylamines. Examples of dopants of this type are substituted or unsubstituted tristilbeneamines or the dopants described in unpublished patent applications DE 102004031000.9, EP 04028407.7 and EP 05001891.0.

The invention furthermore relates to the use of the compounds of the formula (1) or corresponding polymers in organic electronic devices.

The present invention furthermore relates to organic electronic devices containing anode, cathode and at least one organic layer which comprises at least one compound of the formula (1) or a corresponding polymer.

The organic electronic devices are preferably selected from the group of electronic devices consisting of organic and polymeric light-emitting diodes (OLEDs, PLEDs), organic field-effect transistors (O-FETs), organic thin-film transistors (O-TFTs), organic integrated circuits (O-ICs), organic solar cells (O-SCs), organic field-quench devices (O-FQDs), photoreceptors, light-emitting electrochemical cells (LECs) and organic laser diodes (O-lasers). Preference is given to organic and polymeric light-emitting diodes.

The organic electronic device contains one or more organic layers, of which at least one layer comprises at least one compound of the formula (1). If the device is an organic electroluminescent device, at least one organic layer is an emission layer. In the case of organic transistors, at least one organic layer is a charge-transport layer. In organic electroluminescent devices, further layers may be present in addition to the emitting layer. These can be, for example: hole-injection layer, hole-transport layer, charge-blocking layer, electron-transport layer and/or electron-injection layer, each of which may be doped or undoped. However, it should be pointed out at this point that each of these layers must not necessarily be present.

Depending on the precise structure of the compound of the formula (1), this may be used in various functions in the organic electronic device, for example as host material for dopants which emit light from the singlet state or from a state of higher spin multiplicity (for example the triplet state), as dopant, as hole-transport material, as electron-transport material or as hole-blocking material. In a preferred embodiment of the invention, the compound is used as host material. Preferred dopants are selected from the group of the monostyrylamines, distyrylamines, tristyrylamines, tetrastyrylamines and arylamines, as described above.

Preference is furthermore given to an organic electronic device, characterised in that one or more layers are coated by a sublimation process. The materials here are applied by vapour deposition in vacuum sublimation units at a pressure below $10^{-5}$ mbar, preferably below $10^{-6}$ mbar, particularly preferably below $10^{-7}$ mbar.

Preference is likewise given to an organic electronic device, characterised in that one or more layers are coated by the OVPD (organic vapour phase deposition) process or with the aid of carrier-gas sublimation. The materials here are generally applied at a pressure between $10^{-5}$ mbar and 1 bar.

Preference is furthermore given to an organic electronic device, characterised in that one or more layers are produced from solution, such as, for example, by spin coating, or using any desired printing process, such as, for example, screen printing, flexographic printing or offset printing, but particularly preferably by LITI (light induced thermal imaging, thermal transfer printing) or ink-jet printing.

The emitting devices described above have the following surprising advantages over the prior art:
1. The stability of corresponding devices is greater than systems in accordance with the prior art, which is evident, in particular, from a longer lifetime.
2. The sublimation stability of the compounds according to the invention is greater than that of compounds in accordance with the prior art.
3. In contrast to compounds used to date, which were difficult to purify due to their poor solubility, the compounds of the formula (1) are readily soluble and therefore simpler to purify and also simpler to process from solution.
4. Materials in accordance with the prior art in some cases form atropisomers, which result in problems with reproducibility, as already explained above. Through the introduction of at least one bridge $L^1$, only one atropisomer is used in accordance with the invention, meaning that no isomers are present and consequently reproducible production of the device is possible. In particular, the introduction of this bridge also means that re-isomerisation in solution during the preparation and purification of the materials or in the solid or in the gas phase during sublimation is not possible, and consequently problems due to the presence of different isomers cannot occur here.

EXAMPLES

The following syntheses are carried out under a protective-gas atmosphere, unless stated otherwise. The starting materials can be purchased from ALDRICH or ABCR (9,10-dibromoanthracene, 2-formylbenzene-boronic acid, methoxyphenylboronic acid, 2-bromophenol, N-bromo-succinimide (NBS), tetrakistriphenylphosphinopalladium(0), inorganics, solvents). Tetraethyl o-xylyienediphosphonate can be prepared as described in DE 19600304. 9,10-Bis(2,6-dimethoxyphenyl)anthracene can be prepared as described by Zweig et at (*J. Org. Chem.* 1967, 32, 1322). Anthracene-9-boronic acid and anthracene-9,10-bisboronic acid can be prepared as described by Suzuki et al (*Syn. Met.* 2004, 143, 89) and subsequently esterified using ethylene glycol on a water separator (entrainer toluene) (yield: anthracene-9-boronic acid ethylene glycol ester 83.0%, anthracene-9,10-bisboronic acid bisethylene glycol ester 33.7%).

Example 1

Synthesis of Ansa Compound 1 (A1)

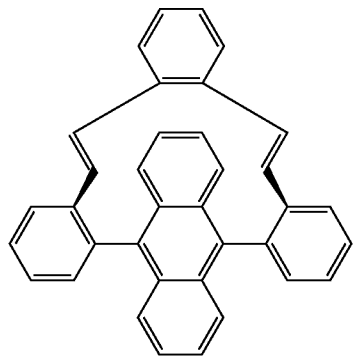

a) 9,10-Bis(2-formylphenyl)anthracene (atropisomer mixture)

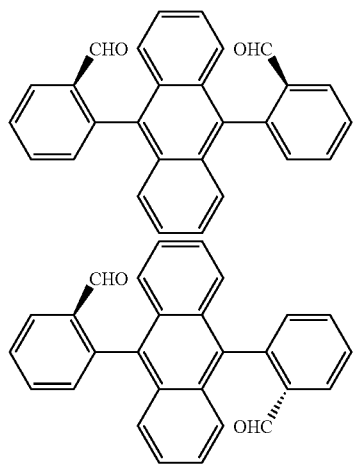

2.3 g (2 mmol) of tetrakistriphenylphosphinopalladium(0) are added to a well-stirred, degassed suspension of 33.6 g (100 mmol) of 9,10-dibromo-anthracene, 45.0 g (300 mmol) of 2-formylbenzeneboronic acid and 55.1 g (520 mmol) of sodium carbonate in a mixture of 500 ml of toluene, 150 ml of ethanol and 400 ml of water, and the mixture is refluxed for 60 h. After cooling, the organic phase is separated off, washed three times with 500 ml of water and once with 500 ml of saturated, aqueous sodium chloride solution and subsequently dried over magnesium sulfate. After the drying agent has been filtered off, the organic phase is evaporated to dryness under reduced pressure in a rotary evaporator. The oily residue obtained in this way is dissolved in 300 ml of chloroform and filtered through a silica-gel frit with suction. After evaporation of the chloroform phase under reduced pressure, the pasty residue is taken up in 200 ml of ethanol and stirred at room temperature for 1 h. The deposited crystals are filtered off with suction, washed with 50 ml of ethanol and subsequently dried under reduced pressure; yield. 24.5 g, 63.4% of theory, 98% according to $^1$H-NMR. According to $^1$H-NMR, this fraction comprises two atropisomers, evident from the two spectroscopically resolved signals of the formyl protons, in the ratio 1.0 ($\delta$=9.43 ppm):1.5 ($\delta$=9.40 ppm). The ethanol mother liquor is concentrated to an oil under reduced pressure; yield: 12.8 g, 33.1% of theory, 97% according to $^1$H-NMR. According to $^1$H-NMR, this fraction comprises two atropisomers in the ratio 1.0 ($\delta$=9.43 ppm):2.9 ($\delta$=9.40 ppm).

b) Ansa Compound 1 (A1)

2.11 g (22 mmol) of sodium tert-butoxide are added at 0° C. to a solution of 2.08 g (5.5 mmol) of tetraethyl o-xylylenediphosphonate in 500 ml of DMF and subsequently stirred at 0° C. for 45 min. A solution of 1.93 g (5 mmol) of 9,10-(2-formylphenyl)anthracene (atropisomer mixture from a)) in 500 ml of DMF is added dropwise to the solution over the course of 1.5 h with vigorous stirring. The reaction mixture is stirred at room temperature for a further 12 h, and a mixture of 1000 ml of water, 50 ml of 1N HCl and 500 ml of ethanol is then added dropwise. The deposited precipitate is filtered off, washed three times with 50 ml of water/ethanol (1:1, v/v) each time, then three times with 50 ml of ethanol each time and dried. The residue is taken up in 3 ml of ethyl acetate, 15 ml of n-hexane are added, and the mixture is stirred for 30 min. After oligomeric and polymeric fractions have been filtered off, the mother liquor is chromatographed on silica gel using n-hexane/ethyl acetate (10:1, v/v). Yield: 371 mg, 16.2% of theory, purity: 99.0% according to HPLC. Sublimation: p 1×10$^{-5}$ mbar, T=340° C.

Example 2

Synthesis of Ansa Compound 2 (A2)

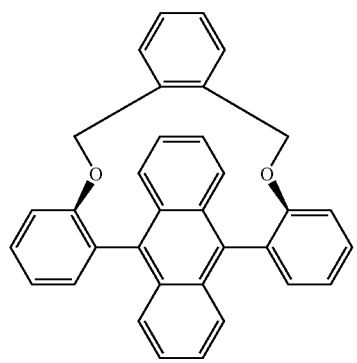

a) 9,10-Bis(2-hydroxyphenyl)anthracene

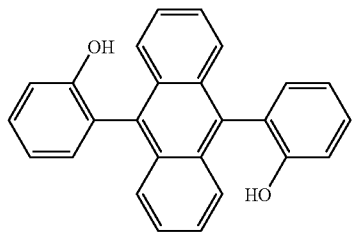

2.3 g (2 mmol) of tetrakistriphenylphosphinopalladium(0) are added to a well-stirred, degassed suspension of 33.6 g (100 mmol) of 9,10-dibromo-anthracene, 45.6 g (300 mmol) of 2-methoxybenzeneboronic acid and 55.1 g (520 mmol) of sodium carbonate in a mixture of 500 ml of 1,2-di-methoxyethane, 150 ml of ethanol and 400 ml of water, and the mixture is refluxed for 60 h. After cooling, the organic phase is separated off, washed three times with 500 ml of water and once with 500 ml of saturated, aqueous sodium chloride solution and subsequently dried over magnesium sulfate. After the drying agent has been filtered off, the organic phase is evaporated to dryness under reduced pressure. The oily residue obtained in this way is dissolved in 300 ml of chloroform and filtered off via a silica-gel frit with suction. After the chloroform phase has been evaporated under reduced pressure, the pasty residue is taken up in 500 ml of NMP, 107.1 g (800 mmol) of lithium iodide (anhydrous) are added, and the mixture is stirred at 190° C. for 24 h. After cooling, the reaction mixture is introduced into 2000 ml of 1N HCl with stirring. The precipitated solid is filtered off and washed three times with 200 ml of water each time and three times with 100 ml of ethanol each time. Finally, the product is recrystallised once from DMSO (10 ml/g) and once from dioxane (20 ml/g) and then dried under reduced pressure. Yield: 24.8 g, 68.4% of theory, purity: 98.0% according to HPLC. The compound does not exhibit the occurrence of atropisomers, evident from the temperature-independent $^1$H-NMR spectrum with singlet for the OH groups, an AA'BB' component of the anthracene protons and an ABCD component of the o-phenylene groups.

b) Ansa Compound 2 (A)

A mixture of 3.62 g (10 mmol) of 9,10-bis(2-hydroxyphenyl)anthracene, 19.74 g (10 mmol) of barium carbonate and 500 ml of DMSO is heated at 100° C. for 30 min. A solution of 1.75 g (10 mmol) of 1,2-bischloromethyl-benzene in 200 ml of DMSO is added dropwise to this mixture over the course of 2 h, and the mixture is subsequently stirred at 100° C. for a further 30 min. After cooling, a mixture of 1000 ml of water and 50 ml of 1N HCl is added. The deposited precipitate is filtered off, washed three times with 50 ml of water/ethanol (1:1, v/v) each time, then three times with 20 ml of ethanol each time and dried. The residue is taken up in 5 ml of ethyl acetate, 20 ml of n-hexane are added, and the mixture is stirred for 30 min. After oligomeric and polymeric fractions have been filtered off, the mother liquor is chromatographed on silica gel using n-hexane/ethyl acetate (10:1, v/v). Yield after drying under reduced pressure: 1.11 g, 23.9% of theory, purity: 99.0% according to HPLC. Sublimation: p=1×10$^{-5}$ mbar, T=340° C.

Example 3

Synthesis of Ansa Compound 3 (A3)

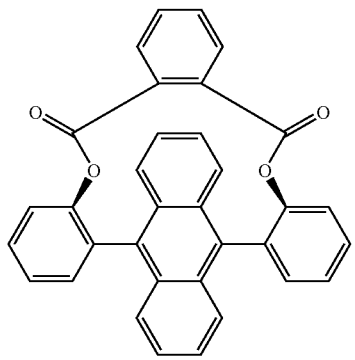

A mixture of 3.62 g (10 mmol) of 9,10-bis(2-hydroxyphenyl)anthracene, 3.30 ml (30 mmol) of 4-methylmorpholine, 50 mg of 4-dimethylamino-pyridine and 300 ml of dioxane is heated to 70° C. A solution of 1.45 ml (10 mmol) of phthaloyl chloride in 200 ml of dioxane is added dropwise to this mixture over the course of 2 h, and the mixture is subsequently stirred at 70° C. for a further 30 min. After cooling, a mixture of 1000 ml of water and 50 ml of 1N HCl is added. The deposited precipitate is filtered off, washed three times with 50 ml of water/ethanol (1:1, v/v) each time, then three times with 30 ml of ethanol each time and dried. The residue is taken up in 5 ml of ethyl acetate, 35 ml of n-hexane are added, and the mixture is stirred for 30 min. After oligomeric and polymeric fractions have been filtered off, the mother liquor is chromatographed on silica gel using n-hexane/ethyl acetate (7:1, v/v). Yield: 1.30 g, 26.4% of theory, purity: 99.0% according to HPLC. Sublimation: $p=1\times10^{-5}$ mbar, T 350° C.

Example 4

Synthesis of Ansa Compound 4 (A4)

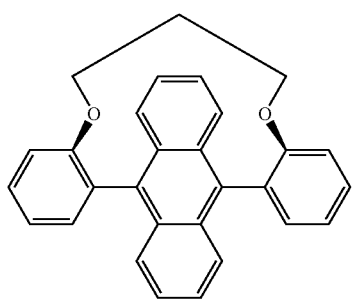

a) 1,3-Bis(2-bromophenyloxy)propane

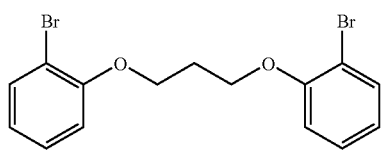

2.6 g (110 mmol) of sodium hydride are added in portions with vigorous stirring to a solution of 18.2 g (105 mmol) of 2-bromophenol in 200 ml of DMF. After the mixture has been stirred for a further 15 min., 1.5 g (10 mmol) of sodium iodide are added. A mixture of 4.8 ml (50 mmol) of 1,3-dibromopropane in 50 ml of DMF is added dropwise to this mixture, which is subsequently stirred at room temperature for 60 h. 5 ml of ethanol are added dropwise to the reaction mixture, which is then poured into 1000 ml of water and extracted three times with 200 ml of dichloromethane. The combined organic phases are washed five times with 500 ml of water, dried over MgSO$_4$ and evaporated under reduced pressure. The foam which remains is washed by stirring with 200 ml of n-heptane, filtered off with suction, washed with n-heptane and dried under reduced pressure. Yield: 15.0 g, 77.7% of theory, purity: 98.0% according to $^1$H-NMR.

b) Ansa Compound 4 (A4)

8.4 ml of n-BuLi (2.5M in n-hexane) are added dropwise with stirring to a solution of 3.86 g (10 mmol) of 1,3-bis(2-bromophenyloxy)propane in 1000 ml of diethyl ether. The reaction mixture is stirred at RT for a further 2 h, then cooled to −78° C., and a solution of 2.10 g (10 mmol) of anthraquinone in 200 ml of THF is subsequently added dropwise. After the mixture has been slowly warmed to room temperature, the solvent is removed under reduced pressure, the residue is taken up in 200 ml of glacial acetic acid, 15.0 g (10 mmol) of sodium iodide and 17.6 g (20 mmol) of sodium hypophosphite hydrate are added, and the mixture is refluxed for 1 h. After cooling, the reaction mixture is poured into 2 l of water and extracted three times with 200 ml of dichloromethane each time. The combined organic phases are washed three times with 500 ml of water each time, subsequently dried over magnesium sulfate and evaporated to dryness under reduced pressure. The residue is taken up in 3 ml of ethyl acetate, 30 ml of n-hexane are added, and the mixture is stirred for 30 min. After oligomeric and polymeric fractions have been filtered off, the mother liquor is chromatographed on silica gel using n-hexane/ethyl acetate (10:1, v/v). Yield: 601 mg, 14.9% of theory, purity: 99.0% according to HPLC.

Example 5

Synthesis of Ansa Compound 5 (A5)

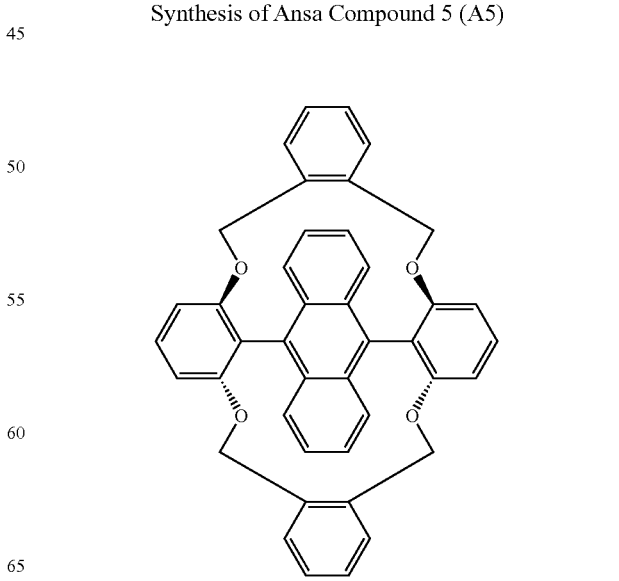

a) 9,10-Bis(2,6-bishydroxyphenyl)anthracene

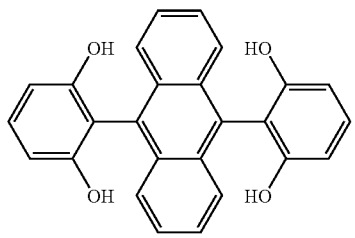

22.5 g (50 mmol) of 9,10-bis(2,6-dimethoxyphenyl)anthracene are dissolved in 500 ml of NMP, 107.1 g (800 mmol) of lithium iodide (anhydrous) are added, and the mixture is stirred at 190° C. for 48 h. After cooling, the reaction mixture is introduced into 2000 ml of 1N HCl with stirring. The precipitated solid is filtered off and washed three times with 200 ml of water each time and then three times with 100 ml of ethanol each time. Finally, the product is recrystallised from DMSO (15 ml/g) and dried under reduced pressure. Yield: 16.9 g, 85.7% of theory, purity: 99.0% according to HPLC.

b) Synthesis of Ansa Compound 5 (A5)

A mixture of 3.94 g (10 mmol) of 9,10-bis(2,6-bishydroxyphenyl)anthracene, 39.5 g (20 mmol) of barium carbonate and 500 ml of DMSO is heated at 100° C. for 30 min. A solution of 3.85 g (22 mmol) of 1,2-bis-chloromethylbenzene in 200 ml of DMSO is added dropwise to this mixture over the course of 2 h, and the mixture is subsequently stirred at 100° C. for a further 30 min. After cooling, a mixture of 1000 ml of water and 50 ml of 1N HCl is added. The deposited precipitate is filtered off, washed three times with 50 ml of water/ethanol (1:1, v/v) each time, then three times with 50 ml of ethanol each time and dried. The residue is chromatographed on silica gel using n-hexane/ethyl acetate (7:1, v/v). Yield after drying under reduced pressure: 2.9 g, 48.4% of theory, purity: 99.0% according to HPLC.

Example 6

Synthesis of Ansa Compound 6 (A6)

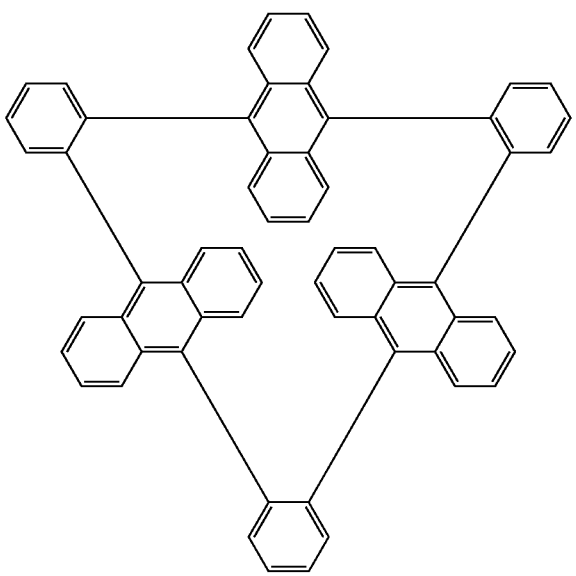

a) 9,10-Bis(2-bromophenyl)anthracene

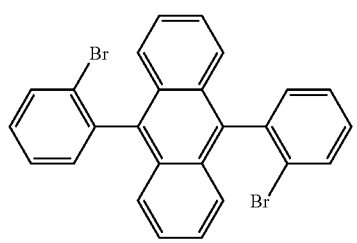

2.9 g (2.5 mmol) of tetrakistriphenylphosphinopalladium (0) are added to a degassed suspension of 121 ml (1.0 mol) of 1,2-dibromobenzene, 79.5 g (250 mmol) of 9,10-anthracenebisboronic acid bisethylene glycol ester and 157 g of potassium fluoride (2.7 mol) in a mixture of 1300 ml of dioxane, 350 ml of ethanol and 950 ml of water, and the mixture is then refluxed for 100 h. After cooling, the crystalline solid is filtered off with suction, washed three times with 200 ml of water/ethanol (1:1, v/v) each time and three times with 100 ml of ethanol each time, dried under reduced pressure and recrystallised from o-dichlorobenzene (5 ml/g). Yield: 38.8 g, 31.8% of theory, purity: 99.0% according to HPLC.

b) 1,2-Bis(anthracen-9-yl)benzene

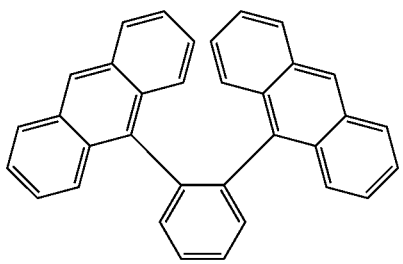

1.6 g (1 mmol) of tetrakistriphenylphosphinopalladium(0) are added to a degassed suspension of 12.1 ml (100 mmol) of 1,2-dibromobenzene, 74.4 g (300 mmol) of 9-anthraceneboronic acid ethylene glycol ester, 58.1 g of potassium fluoride (1 mol) in a mixture of 550 ml of dioxane, 150 ml of ethanol and 400 ml of water, and the mixture is refluxed for 100 h. After cooling, the solid is filtered off with suction, washed three times with 200 ml of water/ethanol (1:1, v/v) each time and three times with 100 ml of ethanol each time and dried under reduced pressure. The solid is suspended in 1000 ml of acetic acid and refluxed for 1 h. The suspension is allowed to cool to 90° C. and is filtered rapidly through a glass suction filter (P3). The filtrate is re-suspended in 700 ml of acetic acid, re-fluxed for 1 h and again filtered with suction while hot. The solid obtained in this way is washed by stirring in 1000 ml of hot ethanol and dried under reduced pressure. Yield: 33.8 g, 78.5% of theory, purity: 97% according to $^1$H-NMR.

c) 1,2-Bis(10-bromoanthracen-9-yl)benzene

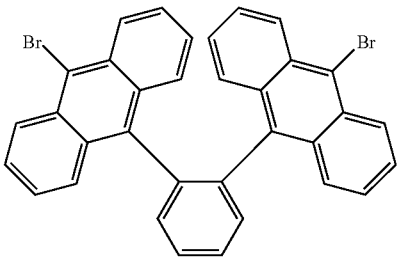

35.6 g (200 mmol) of NBS are added with vigorous stirring at room temperature with exclusion of light to a suspension of 21.5 g (50 mmol) of 1,2-bis(anthracen-9-yl)benzene and 300 g of glass beads (diameter 4 mm) in 500 ml of THF. After the mixture has been stirred for 24 h, a further 17.8 g (100 mmol) of NBS are added, and the mixture is stirred for a further 24 h. The mixture is filtered with suction through a slot frit in order to remove the glass beads, and the latter are rinsed with 500 ml of EtOH. The solid in the mother liquor is filtered off, washed five times with 100 ml of ethanol each time and dried under reduced pressure. Yield: 22.9 g, 77.8% of theory, purity: 97.0% according to $^1$H-NMR (TCE-d2, 90° C.).

d) Synthesis of Ansa Compound 6 (A6)

16.8 ml (42 mmol) of n-BuLi (2.5M in n-hexane) are added dropwise to a suspension, cooled to −78° C., of 4.88 g (10 mmol) of 9,10-bis(2-bromo-phenyl)anthracene and 5.88 g of 1,2-bis(10-bromoanthracen-9-yl)benzene in 1000 ml of THF, and the mixture is stirred at −78° C. for a further 3 h. 6.1 g (45 mmol) of anhydrous copper(II) chloride are then added, and the mixture is stirred at −78° C. for a further 1 h, allowed to warm to room temperature and stirred at 50° C. for a further 16 h. After cooling and addition of 1000 ml of dichloromethane, the mixture is filtered through silica gel, and the organic phase is washed five times with 10% ammonia solution, dried over magnesium sulfate and evaporated under reduced pressure. The residue is taken up in 6 ml of dichloromethane, 30 ml of n-hexane are added, and the mixture is stirred for 30 min. After oligomeric and polymeric fractions have been filtered off, the mother liquor is chromatographed on silica gel using n-hexane/dichloromethane (5:1, v/v). Yield: 730 mg, 9.6% of theory, purity: 99.0% according to HPLC. Sublimation: p=1×10$^{-5}$ mbar, T=300° C.

Example 7

Production of the OLEDs

OLEDs are produced by a general process as described in WO 04/058911, which is matched in individual cases to the particular circumstances (for example layer-thickness variation in order to achieve optimum efficiency or colour).

In the following examples, the results of various OLEDs are presented. The basic structure, the materials and layer thicknesses used, in addition to the emitting layer, are identical in all examples for better comparability. OLEDs having the following structure are produced analogously to the above-mentioned general process:

| Hole-injection layer (HIL) | 60 nm PEDOT (applied by spin-coating from water; purchased from H. C. Starck, Goslar, Germany; poly(3,4-ethylenedioxy-2,5-thiophene)) |
| --- | --- |
| Hole-transport layer (HTL) | 20 nm NaphDATA (applied by vapour deposition; purchased from SynTec, Wolfen, Germany; 4,4',4''-tris(N-1-naphthyl-N-phenyl-amino)triphenylamine) |
| Hole-transport layer (HTL) | 20 nm S-TAD (applied by vapour deposition; prepared as described in WO 99/12888; 2,2',7,7'-tetrakis(diphenylamino)spiro-9,9'-bifluorene) |
| Emission layer (EML) | see Table 1 for materials, concentration and layer thicknesses |
| Electron-transport layer | AlQ$_3$ 10 nm (applied by vapour deposition; AlQ$_3$ purchased from SynTec; tris(quinolinato)aluminium(III)) |
| Ba—Al (cathode) | 3 nm Ba, 150 nm Al on top. |

These as yet unoptimised OLEDs are characterised by standard methods; the electroluminescence spectra, the efficiency (measured in cd/A), the power efficiency (measured in lm/W) as a function of the brightness, calculated from current/voltage/brightness characteristic lines (IUL characteristic lines), and the lifetime are determined for this purpose. The lifetime is defined as the time after which the initial brightness of the OLED at a constant current density of 10 mA/cm$^2$ has dropped to half.

Table 1 shows the results of some OLEDs, along with the composition of the EML including the layer thicknesses. The EMLs contain dopant D1 as emitting materials. The host materials used are compounds V1 and V2 shown below (comparative materials in accordance with the prior art) and ansa compounds A1 to A6 (Examples 1 to 6).

Dopant D1

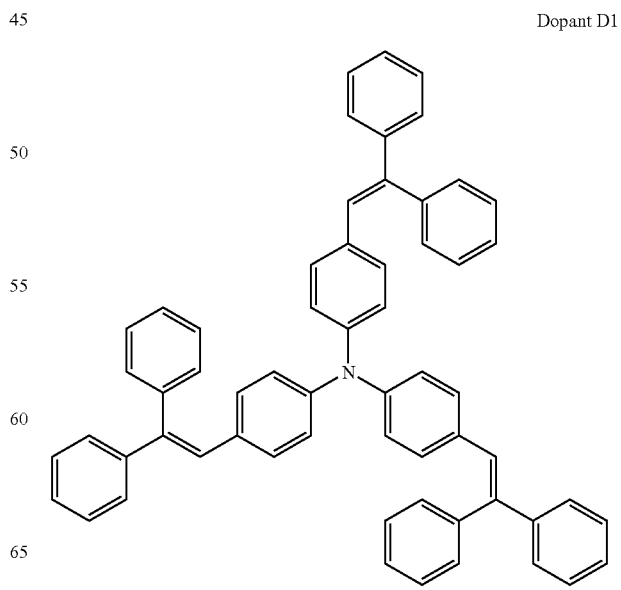

Host V1

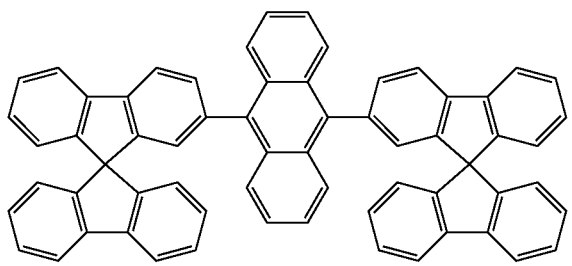

Host V2

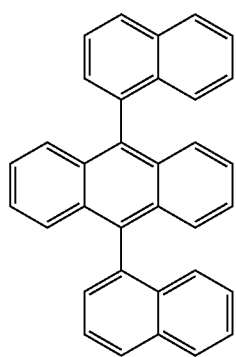

As can be seen from the table, better lifetimes are obtained with the ansa compounds according to the invention than with host materials in accordance with the prior art. Furthermore, ansa compound A6, in particular, in combination with a blue dopant is capable of producing highly efficient white emission from only one emission layer and with a very good lifetime.

The invention claimed is:

1. A compound of formula (1)

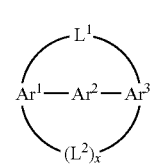

formula (1)

wherein

Ar$^1$ and Ar$^3$ are, identically or differently on each occurrence, an aromatic or heteroaromatic ring system having 6 to 40 aromatic ring atoms, optionally substituted by one or more radicals R;

Ar$^2$ is, identically or differently on each occurrence, selected from the group consisting of anthracene, acridine, phenanthrene, pyrene, naphthacene, chrysene, pentacene, and perylene, wherein said anthracene, acridine, phenanthrene, pyrene, naphthacene, chrysene, pentacene, and perylene are optionally substituted by R, with the proviso that Ar$^1$ and Ar$^3$ are not linked to Ar$^2$ via adjacent positions or peri-positions;

L$^1$ and L$^2$ are, identically or differently on each occurrence, a divalent organic bridge containing up to 60 C atoms, optionally substituted by one or more radicals R;

R is, identically or differently on each occurrence, H; F; Cl; Br; I; CN; NO$_2$; COOR$^1$; B(OR$^1$)$_2$; B(R$^1$)$_2$; Si(R$^1$)$_3$; a straight-chain alkyl or alkoxy having up to 40 C atoms; a branched or cyclic alkyl or alkoxy having 3 to 40 C atoms, optionally substituted by R$^1$, wherein one or more non-adjacent C atoms of said straight-chain alkyl or alkoxy or said branched or cyclic alkyl or alkoxy are optionally replaced by N—R$^1$, O, S, O—CO—O, CO—O, —CR$^1$=CR$^1$—, or —C≡C—, and wherein one or more H atoms of said straight-chain alkyl or alkoxy or said branched or cyclic alkyl or alkoxy are optionally replaced by F, Cl, Br, I, or CN; or an aromatic or heteroaromatic ring system having 5 to 40 aromatic ring atoms, optionally substituted by one or more radi-

TABLE 1

| Example | EML | Max. efficiency (cd/A) | Voltage (V) at 100 cd/m$^2$ | CIE | Lifetime (h) |
|---|---|---|---|---|---|
| Example 7a (comparison) | V1:D1 (5%) (30 nm) | 4.8 | 5.3 | x = 0.18; y = 0.30 | 3800 |
| Example 7b (comparison) | V2:D1 (5%) (30 nm) | 7.9 | 5.3 | x = 0.17; y = 0.31 | 15000 |
| Example 7c | A1:D1 (5%) (30 nm) | 8.3 | 5.1 | x = 0.18; y = 0.29 | 17000 |
| Example 7d | A2:D1 (5%) (30 nm) | 7.7 | 5.2 | x = 0.18; y = 0.30 | 16500 |
| Example 7e | A3:D1 (5%) (30 nm) | 8.2 | 5.4 | x = 0.18; y = 0.29 | 15000 |
| Example 7f | A4:D1 (5%) (30 nm) | 8.6 | 5.2 | x = 0.18; y = 0.30 | 19000 |
| Example 7g | A5:D1 (5%) (30 nm) | 8.5 | 4.9 | x = 0.17; y = 0.29 | 22500 |
| Example 7h | A6:D1 (5%) (30 nm) | 12.4 | 4.6 | x = 0.35; y = 0.37 | 21000 | cals $R^1$; or a combination of two, three or four of these systems; and wherein two or more R optionally define a further mono- or polycyclic, aliphatic or aromatic ring system;

$R^1$ is, identically or differently on each occurrence, H or an aliphatic or aromatic hydrocarbon radical having up to 20 C atoms; wherein two or more $R^1$ optionally define a ring system;

x is, identically or differently on each occurrence, 0 or 1, wherein when x is 0, $L^2$ is not present.

2. The compound of claim 1, wherein $Ar^1$ and $Ar^3$ are linked in such a way that at least four aromatic ring atoms of unit $Ar^2$ are located between $Ar^1$ and $Ar^3$.

3. The compound of claim 1, wherein $Ar^1$ and $Ar^3$, identically or differently on each occurrence, are aromatic ring systems having 6 to 40 C atoms or heteroaromatic ring systems having 2 to 40 C atoms and at least one heteroatom, with the proviso that the total number of C atoms and heteroatoms is at least 5, and wherein said aromatic ring systems or heteroaromatic ring systems are optionally substituted by R.

4. The compound of claim 1, wherein $L^1$ and, if present, $L^2$ are linked to $Ar^1$ and $Ar^3$ respectively in the ortho-position to the link to $Ar^2$.

5. The compound of claim 1, wherein $Ar^1$ and $Ar^3$ are identical.

6. The compound of claim 1, wherein $L^1$ and $L^2$ are selected from the groups consisting of alkenes, aromatic groups containing 6 to 40 C atoms, heteroaromatic groups containing 2 to 40 C atoms, imines, alkoxy groups, thioalkoxy groups, aryloxy groups, thioaryl groups, amines, arylamines, alkylenes, arylboranes, and combinations thereof.

7. The compound of claim 1, wherein the length of $L^1$ and $L^2$ is selected so that a substantially stress-free system is formed.

8. Conjugated, partially conjugated, or non-conjugated polymers, oligomers or dendrimers comprising repeating units of the compound of claim 1.

9. A mixture comprising at least one compound according to claim 1 and one or more compounds selected from the group consisting of monostyrylamines, distyrylamines, tristyrylamines, tetrastyrylamines, and arylamines.

10. An organic electronic device comprising an anode, a cathode, and at least one organic layer comprising at least one compound according to claim 1.

11. The organic electronic device of claim 10, wherein said device is selected from the group consisting of organic and polymeric light-emitting diodes, organic field-effect transistors, organic thin-film transistors, organic integrated circuits, organic solar cells, organic field-quench devices, and organic laser diodes.

12. The organic electronic device of claim 10, wherein said device comprises dopants selected from the group consisting of monostyrylamines, distyrylamines, tristyrylamines, tetrastyrylamines, and arylamines.

* * * * *